United States Patent [19]
Arnold, Jr. et al.

[11] Patent Number: 6,031,091
[45] Date of Patent: *Feb. 29, 2000

[54] NON-NUCLEOTIDE LINKING REAGENTS FOR NUCLEOTIDE PROBES

[75] Inventors: Lyle J. Arnold, Jr., Poway, Calif.; Mark A. Reynolds, Lafayette, Colo.; Ram S. Bhatt, San Diego, Calif.

[73] Assignee: Gen-Probe Incorporated, San Diego, Calif.

[21] Appl. No.: 08/908,535

[22] Filed: Aug. 7, 1997

Related U.S. Application Data

[60] Continuation-in-part of application No. 08/485,629, Jun. 7, 1995, Pat. No. 5,696,251, which is a division of application No. 08/182,666, Jan. 14, 1994, Pat. No. 5,585,481, which is a continuation of application No. 07/319,422, Mar. 6, 1989, abandoned, which is a continuation-in-part of application No. 07/099,050, Sep. 21, 1987, abandoned.

[51] Int. Cl.$^7$ .............................. C07H 21/00; C07F 9/02
[52] U.S. Cl. .................. 536/25.34; 536/23.1; 536/24.3; 536/24.31; 536/24.32; 536/25.33; 558/70; 558/199; 558/202; 562/8; 562/10; 562/23
[58] Field of Search .................... 536/23.1, 24.3, 536/24.31, 24.32, 25.33, 25.34; 558/70, 199, 202; 562/8, 10, 23

[56] References Cited

U.S. PATENT DOCUMENTS

| | | |
|---|---|---|
| 4,415,732 | 11/1983 | Caruthers et al. . |
| 4,500,707 | 2/1985 | Caruthers et al. . |
| 4,599,303 | 7/1986 | Yabusaki et al. . |
| 4,725,677 | 2/1988 | Koster et al. . |
| 4,757,141 | 7/1988 | Fung et al. . |
| 4,835,263 | 5/1989 | Nguyen et al. . |
| 4,968,742 | 11/1990 | Lewis et al. . |
| 5,039,796 | 8/1991 | Engels et al. . |
| 5,071,974 | 12/1991 | Groody et al. . |
| 5,324,831 | 6/1994 | Marquez et al. . |
| 5,585,481 | 12/1996 | Arnold, Jr. et al. . |
| 5,696,251 | 12/1997 | Arnold, Jr. et al. . |

*Primary Examiner*—James O. Wilson
*Attorney, Agent, or Firm*—Lyon & Lyon LLP

[57] ABSTRACT

A versatile reagent with a non-nucleotide monomeric unit having a ligand, and first and second coupling groups which are linked to the non-nucleotide monomeric unit. The ligand can be either a chemical moiety, such as a label or intercalator, or a linking arm which can be linked to such a moiety. Such reagent permits preparation of versatile nucleotide/non-nucleotide polymers, having any desired sequence of nucleotide and non-nucleotide monomeric units, each of the latter of which bear a desired ligand. These polymers can for example, be used as probes which can exhibit enhanced sensitivity and/or which are capable of detecting a genus of nucleotides each species of which has a common target nucleotide sequence of interest bridged by different sequences not of interest.

32 Claims, 20 Drawing Sheets

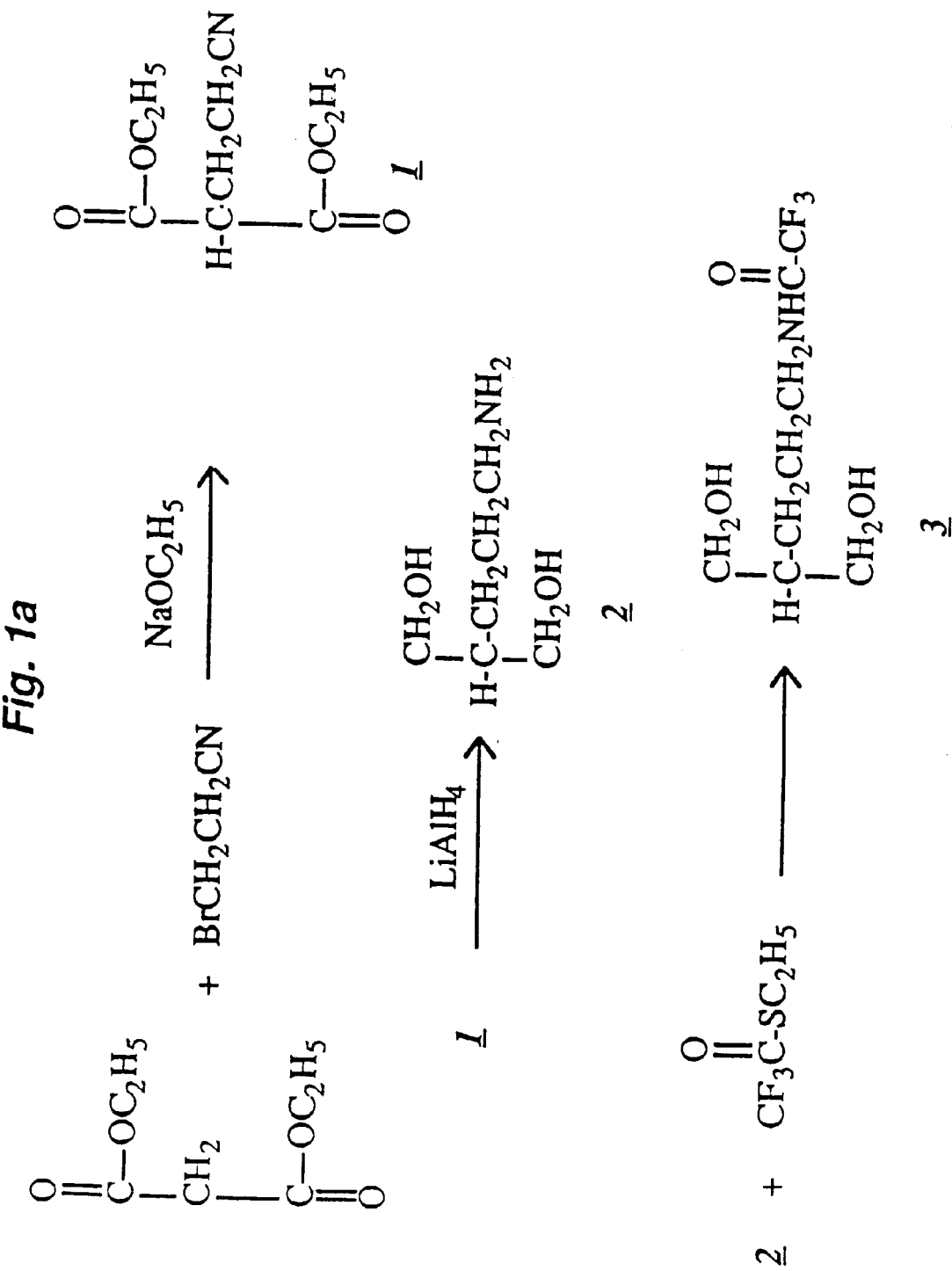

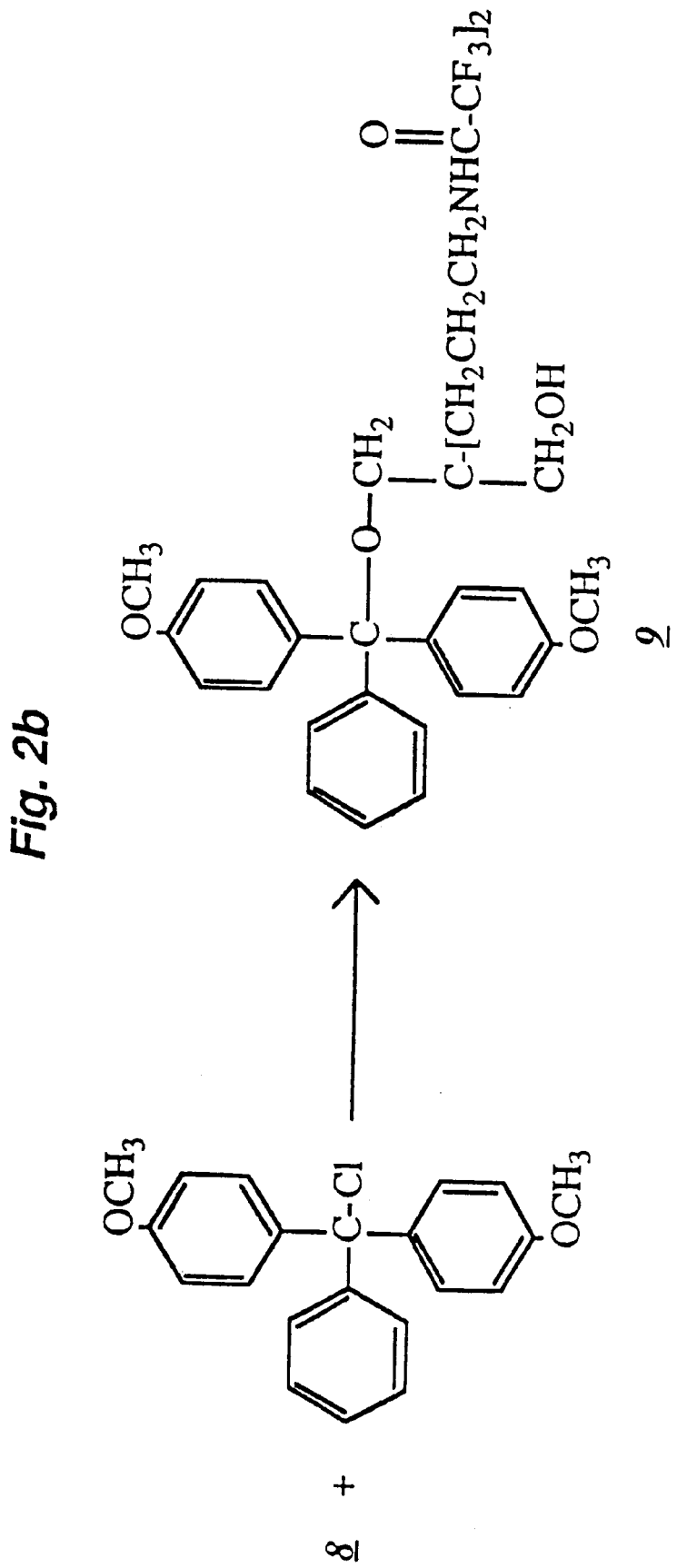

21  n=1
22  n=3
23  n=5

NON-NUCLEOTIDE LINKING REAGENTS FOR NUCLEOTIDE PROBES

CROSS REFERENCES TO RELATED APPLICATIONS

This application is a continuation-in-part of U.S. Ser. No. 08/485,629, filed Jun. 7, 1995, now U.S. Pat. No. 5,696,251, which is a divisional of U.S. Ser. No. 08/182,666, filed Jan. 14, 1994, now U.S. Pat. No. 5,585,481, which is a continuation of U.S. Ser. No. 07/319,422, filed Mar. 6, 1989, now abandoned, which is a continuation-in-part of U.S. Ser. No. 07/099,050, filed Sep. 21, 1987, now abandoned. U.S. Ser. Nos. 08/485,629, 08/182,666, 07/319,422 and 07/099,050 are incorporated by reference herein in their entirety, including claims, drawings and sequences.

FIELD OF THE INVENTION

This invention relates to non-nucleotide reagents which can conveniently allow single or multiple moieties, such as labels or intercalators, to be linked to a nucleotide probe, at any specific pre-selected location(s) thereon.

TECHNOLOGY REVIEW

In clinical research and diagnosis, a known technique for determining the presence of a particular nucleotide sequence (the "target nucleotide sequence" or simply the "target sequence") in either RNA or DNA, is to perform a nucleic acid hybridization assay. In such an assay, a nucleotide multimer probe (typically an oligonucleotide) is chosen which has a nucleotide sequence complimentary to at least a portion of the target sequence. Typically, the probe is labelled, that is, it is provided with an atom or a group linked thereto, the presence of which can be readily detected. When the labelled probe is exposed to a test sample suspected of containing the target nucleotide sequence, under hybridizing conditions, the target will hybridize with any such labelled probe. The presence of the target sequence in the sample can be determined qualitatively or quantitatively usually by separating hybridized and non-hybridized probe, then determining the amount of labelled probe which hybridized, either by determining the presence of label in probe hybrids, or by determining the quantity of label in non-hybridized probes.

Historically, radioactive labels were used. However, due to difficulties in handling, non-isotopic labels were later developed. Such labels include those whose presence is determined either directly or indirectly. Examples of direct labels include chemiluminescence, phosphorescent, fluorescent, or spectroscopically detectable labels. Examples of indirect labels include compounds such as biotin and various antigens which can be detected by means of proteins conjugated to an appropriate detectable label.

Some prior methods for linking a label to a nucleotide probe have typically been based upon linking a single label to a nucleotide, then incorporating one or more of those nucleotides into the probe. For example, analogs of dUTP and UTP containing a biotin moiety attached to the C-5 position of the pyrimidine ring, have been chemically synthesized and incorporated enzymatically into polynucleotides (P. R. Langer et al., Proc. Nat. Acad. Sci., U.S.A., Vol. 78, p. (6633, 1981). Such biotin labelled nucleotides may be incorporated into nucleic acid probes of biological or synthetic origin by enzymatic procedures. In addition, the 5'-allylamine precursors of the forgoing analogs have been suggested for use in a similar manner, leading to incorporation of nucleophilic amine moieties into the probe, which could be linked to labels using common methods. Other deoxynucleotide triphosphate analogs have been incorporated enzymatically into probes. Specifically, bromo-dUTP and iodo-dUTP have been incorporated and detected immunochemically (Boultwood, J. et al., J. Pathol., Vol. 148, p. 61, 1986). In addition, 4-thio-UTP (H. Eshaghpour et al., Nucl. Acids Res., Vol. 7, p. 1485, 1979), has been attached to the 3'-end of DNA fragments and subsequently labelled at its nucleophilic sulfhydryl moiety. A PCT application by Tchen (international publication number WO 86/00074; published Jan. 3, 1986), discloses a technique in which apparently random pyrimidine base nucleotides can be depyrimidated, and the resulting sugar rings opened so that an amine bearing moiety can be attached thereto.

Chemical methods for labelling have also been proposed, which essentially allow labels to be randomly linked to some nucleotides in a nucleotide multimer. For example, N-acetoxy-N-acetylaminofluorene has been coupled to guanine residues of nucleic acids and subsequently detected by immunochemical techniques (P. Chen et al., Proc. Nat. Acad. Sci. U.S.A., Vol. 81, p. 3466, 1984). Another such method, which provides a nucleophilic amine group to which a label can be linked, involves bisulfite catalyzed transamination at the C-6 position of cytosine residues of nucleic acid probes (R. P. Viscidi et al., J. Clin. Biol., Vol. 23, p. 311, 1986). Both the chemical and enzymatic methods described above suffer from the fact that either single nucleotides cannot be specifically labelled or the procedure modifies the exocyclic amines on the nucleotide bases and thus interfere with hybridization.

Other techniques have been disclosed, which allow attachment of only a single label at the 5' or 3' end of a nucleotide multimer, typically an oligonucleotide. For example, such a technique is disclosed by C. F. Chu et al., Nucl. Acids Res., Vol. 11, p. 6513, 1983, and by A. Chollet et al., Nucl. Acids Res., Vol. 13, p. 1529, 1985. Similar terminal labelling approaches have been disclosed, which are more amenable to label attachment as a final step in solid-phase oligonucleotide synthesis. For example, see B. A. Connolly, Nucl. Acids Res., Vol. 13, p. 4485, 1985; S. Agrawal et al., Nucl. Acids Res., Vol. 14, p. 6227, 1986; and B. A. Connolly, Nucl. Acids Res., Vol. 15, p. 3131, 1987. However, these terminal labelling methods are limited in that they only allow attachment of a single-label at the end of the nucleotide multimer.

Compounds have been suggested which can be used to insert a primary amine-modified nucleotide residue at selected positions in a synthetic oligonucleotide during standard automated synthesis procedures. Such compounds include analogs of deoxythymidine, deoxyadenine, deoxyquanine, and deoxycytidine (G. B. Dreyer et al., Proc. Natl. Acad. Sci., U.S.A., Vol. 82, p. 968, 1985; J. L. Ruth, PCT application Publication No. WO 84/03285 published Aug. 30, 1984). Theoretically, such compounds might allow for labelled nucleotides to be placed at a number of sites along a sequence, thus permitting use of multiple labels to increase sensitivity of detection. However, it has been demonstrated that use of such labelled nucleotides in a probe can reduce the stability of a hybrid formed with a target sequence particularly when multiple labels are present. Such reduced hybrid stability has been shown for nucleic acid probes of biological origin possessing multiple biotin moieties attached to either uridine, cytidine or adenine bases (R. P. Viscidi et al., J. Clin. Microbiol., Vol. 23, p. 311, 1986; G. Gebeyehu et al., Nucl. Acids Res., Vol. 15 p. 4513, 1987). Reduced hybrid stability has also been reported for synthetic oligonucleotides possessing multiple fluorescein labels attached to modified uridine residues (J. Haralambidis, et al., Nucl. Acids Res., Vol. 15, p. 4857, 1987). Such instability can also be demonstrated for synthetic oligonucleotides possessing biotin and fluorescein labels attached to the N-4 position of the cytidine bases. Furthermore, in order to place a label or labels at any desired position(s) within synthetic oligonucleotide, it would be necessary to have a total of eight different compounds (four for deoxyribonucleotide multimers, and four for ribonucleotide multimers).

In addition, derivatives of nucleotide linking phosphate groups have been disclosed, the nucleophilic moiety of which can be labeled following their incorporation into an oligonucleotide (R. L. Letsinger and M. E. Schott, J. Am. Chem. Soc. 1981, Vol. 103, p. 7394; Japanese patents to N. Sugimoto, Nos. 61 44,353; 61 57,595; 61 44,352, all issued March 1986). However, such compounds being based on nucleotide derivatives, would exhibit at least some of the disadvantages discussed above for nucleotide based derivatives. Further, the linker examples disclosed in the foregoing, could not be used in presently standard solid-phase synthesis techniques, without modification of such techniques.

DEFINITIONS

As used in this disclosure and claims, the following terms are defined as:

nucleotide: a subunit of a nucleic acid consisting of a phosphate group, a 5 carbon sugar and a nitrogen containing base. In RNA the 5 carbon sugar is ribose. In DNA, it is a 2-deoxyribose. The term also includes analogs of such subunits.

nucleotide multimer: a chain of nucleotides linked by phosphodiester bonds, or analogs thereof.

oligonucleotide: a nucleotide multimer generally about 10 to about 100 nucleotides in length, but which may be greater than 100 nucleotides in length. They are usually considered to be synthesized from nucleotide monomers, but may also be obtained by enzymatic means.

deoxyriboligonucleotide: an oligonucleotide consisting of deoxyribonucleotide monomers.

polynucleotide: a nucleotide multimer generally about 100 nucleotides or more in length. These are usually of biological origin or are obtained by enzymatic means.

nucleotide multimer probe: a nucleotide multimer having a nucleotide sequence complementary with a target nucleotide sequence contained within a second nucleotide multimer, usually a polynucleotide. Usually the probe is selected to be perfectly complementary to the corresponding base in the target sequence. However, in some cases it may be adequate or even desireable that one or more nucleotides in the probe not be complementary to the corresponding base in the target sequence. Typically, the probe is labeled.

non-nucleotide monomeric unit: refers to a monomeric unit which does not significantly participate in hybridization of a polymer. Such monomeric units must not, for example, participate in any significant hydrogen bonding with a nucleotide, and would exclude monomeric units having as a component, one of the 5 nucleotide bases or analogs thereof;

nucleotide/non-nucleotide polymer: a polymer comprised of nucleotide and non-nucleotide monomeric units. When used as a probe, it would typically be labelled.

oligonucleotide/non-nucleotide multimer: a multimer generally of synthetic origin having less than 100 nucleotides, but which may contain in excess of 200 nucleotides and which contains one or more non-nucleotide monomeric units.

monomeric unit: a unit of either a nucleotide reagent or a non-nucleotide reagent of the present invention, which the reagent contributes to a polymer.

hybrid: the complex formed between two nucleotide multimers by Watson-Crick base pairings between the complementary bases.

SUMMARY OF THE INVENTION

The present invention provides a non-nucleotide reagent, with a non-nucleotide monomeric unit which can be coupled synthetically with specific nucleotide monomeric units from nucleotide reagents, to produce a defined sequence polymer with a backbone comprised of nucleotide and non-nucleotide monomeric units. Said non-nucleotide reagent also possesses a ligand which is either a linker-arm moiety which may participate in conjugation reactions once the linker-arm has been deprotected, or it may be a side-arm to which a useful desired chemical moiety has been attached prior to initiating the synthesis of the polymer. In general, the techniques for linking moieties to the linker arm may be similar to the techniques for linking labels to groups on proteins. However, modifications of such techniques may be required. Examples of useful chemistries include the reaction of alkylamines with active esters, active imines, arylflourides, or isothiocyanates, and the reaction of thiols with maleimides, haloacetyls, etc. (for further potential techniques see G. M. Means and R. E. Feeney, "Chemical Modification of Proteins", Holden-Day Inc., 1971; R. E. Feeney, Int. J. Peptide Protein Res., Vol. 29, 1987, p. 145–161). Suitable protecting groups which can be used to protect the linker arm functional group during formation of a polymer are also similar to those used in protein chemistry (see for example, "The Peptides Analysis, Synthesis, Biology," Vol. 3, ed. E. Gross and J. Meienhofer, Academic Press, 1971).

Due to the chemical nature of the non-nucleotide reagent, it may be placed at any desired position within the backbone sequence. This makes it possible to design a wide variety of properties into polymers which contain nucleotide monomers. These include: (1) attachment of specific chemical moieties at any desired location within the polymer, such moieties can include (but are not limited to) detectable labels, intercalating agents, chelators, drugs, hormones, proteins, peptides, haptens, radical generators, nucleolytic agents, proteolytic agents, catalysts, receptor binding substances, and other binding substances of biological interest, and agents which modify DNA transport across a biological barrier (such as a membrane), and substances which alter solubility of a nucleotide multimer. This means that it is possible to position such labels and intercalating agents adjacent to any desired nucleotide; (2) the ability to immobilize the defined sequence to a solid support employing its linker-arm for conjunction to a chemical moiety of said support in order to construct, for example, nucleotide affinity supports; (3) the ability to attach multiple chemical moieties to the polymer through linker-arms by incorporating multiple non-nucleotide monomeric units into the polymers; (4) the ability to construct polymers which differ from naturally occurring polynucleotides in that they have altered activities with proteins and enzymes which act on polynucleotides. For example, the placement of the non-nucleotide monomeric unit on the 3' terminus of an otherwise pure polynucleotide imparts resistance to degradation by snake venom phosphodiesterase. Such non-nucleotide monomeric units may create specific cleavage sites for other nucleases; (5) the ability to construct hybridization probes by interspersing hybridizable nucleotide monomeric units and non-nucleotide monomeric units. For example, a mixed block synthesis of nucleotide and non-nucleotide monomers can be produced, whereby a defined sequence of nucleotide monomers are synthesized followed by a stretch of the one or more non-nucleotide monomeric units followed by second block of defined sequence nucleotide monomers; (6) the ability to construct synthetic probes which simultaneously detect target nucleotide multimers which differ by one or more base pairs. This is accomplished by using the non-nucleotide reagent described herein to replace the nucleotides in the probe with non-nucleotide monomeric units at sites where differences occur in the nucleotide sequence of the various target nucleotide multimers.

In a preferred form of the invention labelled hybridization probes are constructed with a defined sequence comprised of nucleotide and non-nucleotide monomers. In another preferred form of the invention, the non-nucleotide monomeric units are used to connect two or more defined sequence nucleotide multimers, and the non-nucleotide monomeric units are chemically labelled for use in hybridization reactions.

In yet another preferred embodiment, the non-nucleotide reagent is constructed in a manner to permit it to be added in a step-wise fashion to produce a mixed nucleotide/non-nucleotide polymer employing one of the current DNA synthesis methods. Such nucleotide and non-nucleotide reagents normally add in a step-wise fashion to attach their corresponding monomeric units to a growing oligonucleotide chain which is covalently immobilized to a solid support. Typically, the first nucleotide is attached to the support through a cleavable ester linkage prior to the initiation of synthesis. Step-wise extension of the oligonucleotide chain is normally carried out in the 3' to 5' direction. For standard DNA and RNA synthesis methods, see for example "Synthesis and Applications of DNA and RNA" ed. S. A. Narang, Academic Press, 1987, and M. J. Gait, "Oligonucleotide Synthesis", IRL Press, Wash. D.C. U.S.A., 1984. When synthesis is complete, the polymer is cleaved from the support by hydrolyzing the ester linkage mentioned above and the nucleotide originally attached to the support becomes the 3' terminus of the resulting oligomer. By analogy an alternate way to introduce a non-nucleotide monomeric unit is to similarly attach it to a DNA synthesis support prior to initiation of DNA synthesis. In a preferred embodiment the non-nucleotide monomeric unit is attached to a DNA synthesis support through an ester linkage formed using the free alcohol form of the non-nucleotide monomer.

Accordingly, the present invention provides a reagent for preparing polymers which contain a mixture of nucleotide and non-nucleotide monomeric units. Said non-nucleotide monomers additionally contain one or more protected linker-arms or one or more linker-arms conjugated to a desired chemical moiety such as a label or intercalating agent.

Such a non-nucleotide monomer additionally possesses two coupling groups so as to permit its step-wise inclusion into a polymer of nucleotide and non-nucleotide monomeric units. A first one of said coupling groups has the property that it can couple efficiently to the terminus of a growing chain of monomeric units. The second of said coupling groups is capable of further extending, in a step-wise fashion, the growing chain of mixed nucleotide and non-nucleotide monomers. This requires that the second coupling group be inactivated while the first coupling group is coupling, so as to not to substantially couple at that time, but can thereafter be activated so as to then couple the non-nucleotide monomeric unit. The "inactivation" is preferably accomplished with a protecting group on the second coupling group, which can be removed to "activate" the second coupling group. However, it is within the scope of the invention that such "inactivation" and "activation" might be accomplished simply by changing reaction conditions (e.g., pH, temperature, altering the concentration of some other component in the reaction system) with second coupling groups of a suitable chemical structure, which also lend themselves to inactivation and activation by such techniques. Said coupling groups permit the adjacent attachment of either nucleotide or non-nucleotide monomeric units. In a preferred embodiment said coupling groups operate through coupling and deprotection steps which are compatible with one of the standard DNA synthesis methods.

Such methods require that synthesis occur unidirectionally and that all coupling cleavage and deprotection steps occur under "non-adverse" conditions, that is they do not substantially adversely affect the polymer skeleton and its sugar, base, linker-arm and label components nor the monomeric reagents. One skilled in the art can readily identify functionalities, coupling methods, deprotection procedures, and cleavage conditions which meet these criteria (see, for example, the Gait reference, supra).

The non-nucleotide monomer preferably has a skeleton, to the ends of which the coupling groups are linked. The skeleton is preferably an acyclic one to twenty atom chain, and preferably an acyclic hydrocarbon chain of from one to twenty carbon atoms.

In one embodiment of the invention, the reagent is selected from either one of compounds I or II below:

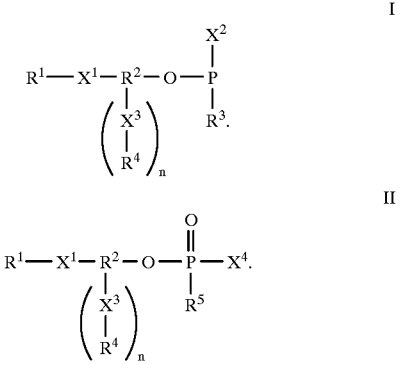

Whether I or II is selected, the described groups are as follows:

(i) $R_2$=the non-nucleotide skeleton;

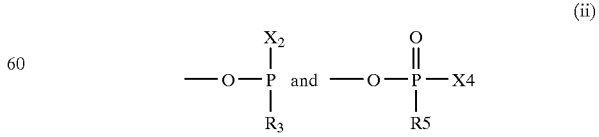

are first coupling groups in which:
$X_2$=halogen or substituted amino
$X4$=halogen; amino; or $O^-$ R₃=alkyl; alkoxy; or phenoxy R5=alkyl; alkoxy; or aryloxy or may be H only if X4=O⁻

(iii) R₁—X₁— is the protected second coupling group in which:

X₁=O; S; NH; or HN=N—

R₁=the protecting group cleavable under coupling group deprotecting conditions to recover the second coupling group H—X₁—;

(iv) n is an integer;

(v) R₄—X3— is the ligand; which is preferably selected from a chemical moiety, or from a protected linking arm which can be deprotected under non-adverse conditions so as to be capable of then linking with a chemical moiety (again under non-adverse conditions). In the case of the latter X₃ is the linking arm and R₄ is the protecting group.

More preferably, some of the groups indicated are as follows:

X₂=Cl; or secondary amino (preferably selected from dialkylamino, and heterocyclic N-amines)

R₃=methoxy; ethoxy; chlorophenoxy; or beta-cyanoethoxy

R₄—X₃=terminates with O;S; NH; or HN=N—; and preferably has a 1 to 25 atom chain extending from R₂

X4=Cl; secondary amino; or O⁻

R5=methoxy; ethoxy; monochlorophenoxy; or beta-cyanoethoxy; or may be H only if X4=O⁻

X₂ is further preferably diisopropylamino, dimethyl amino, or morpholino. R1 is further preferably triphenylmethyl (which includes derivatives thereof, typically dimethoxytriphenylmethyl) and X₁ is O.

R₂ preferably has a secondary carbon attached to the —O—. This allows use of a secondary alcohol during synthesis, which has the advantage of producing a higher yield of the protected reagents from the alcohol.

A method of preparing a nucleotide/non-nucleotide polymer is also described. Such a method comprises using a reagent with a non-nucleotide monomeric unit and a liquid (as described above) bonded thereto, and coupling the non-nucleotide monomeric unit under non-adverse conditions to a first monomeric unit, and to either one of a second additional monomeric unit or a solid support. At least one of the foregoing additional monomeric units is a nucleotide monomeric unit. Should another monomeric unit from a non-nucleotide reagent be chosen, it is of course possible to then couple that monomeric unit to still another non-nucleotide monomeric unit, and so on. Typically, the foregoing couplings are accomplished through a first coupling group and a protected second coupling group, both linked to the non-nucleotide monomeric unit. Thus, the non-nucleotide monomeric unit is first coupled to a first nucleotide monomeric unit through the first coupling group, and the second coupling group then deprotected so as to then couple the non-nucleotide monomeric unit to either of a second nucleotide or another reagent non-nucleotide monomeric unit. The preferred chemical compositions of the reagents which may be used in such a method, are described above.

Products resulting from the above reagents and methods are also described.

Polymeric probes are also disclosed which comprise a plurality of nucleotide and non-nucleotide monomeric units, and at least one acridinium ester label moiety, which typically will serve as a label, linked to a corresponding monomeric unit of the probe.

Preferably the acridinium ester moiety is a chemiluminescent acridinium ester label. There is also disclosed a method of making such probes, comprising linking at least one of such acridinium ester moieties to a corresponding monomeric unit of a polymer having a plurality of nucleotide monomeric units.

DRAWINGS

Embodiments of the invention will now be described with reference to the drawings, in which:

FIGS. 1a to 1c illustrate the preparation of a reagent of the present invention;

FIGS. 2a to 2c illustrate the preparation of another reagent of the present invention.

DETAILED DESCRIPTION OF EMBODIMENTS OF THE INVENTION

The synthesis of three different "linker" reagents of the present invention, will now be described in detail in Examples 1–3 below. Example 4 below, illustrates methods of the present invention, for preparing substituted nucleotides (in particular oligonucleotides), which have the skeleton of the reagent coupled at various specific preselected locations, on the oligonucleotide. Example 5 illustrates linking of a label to a linking group in a substituted nucleotide of the present invention, while Example 6 illustrates a further advantage which can be provided by substituted nucleotides of the present invention, namely resistance to hydrolysis catalyzed by a phosphodiesterase.

EXAMPLE 1

Synthesis of 2-(3-Aminopropyl)-1,3-Dihydroxypropane Linker Reagent

Figure 1B:
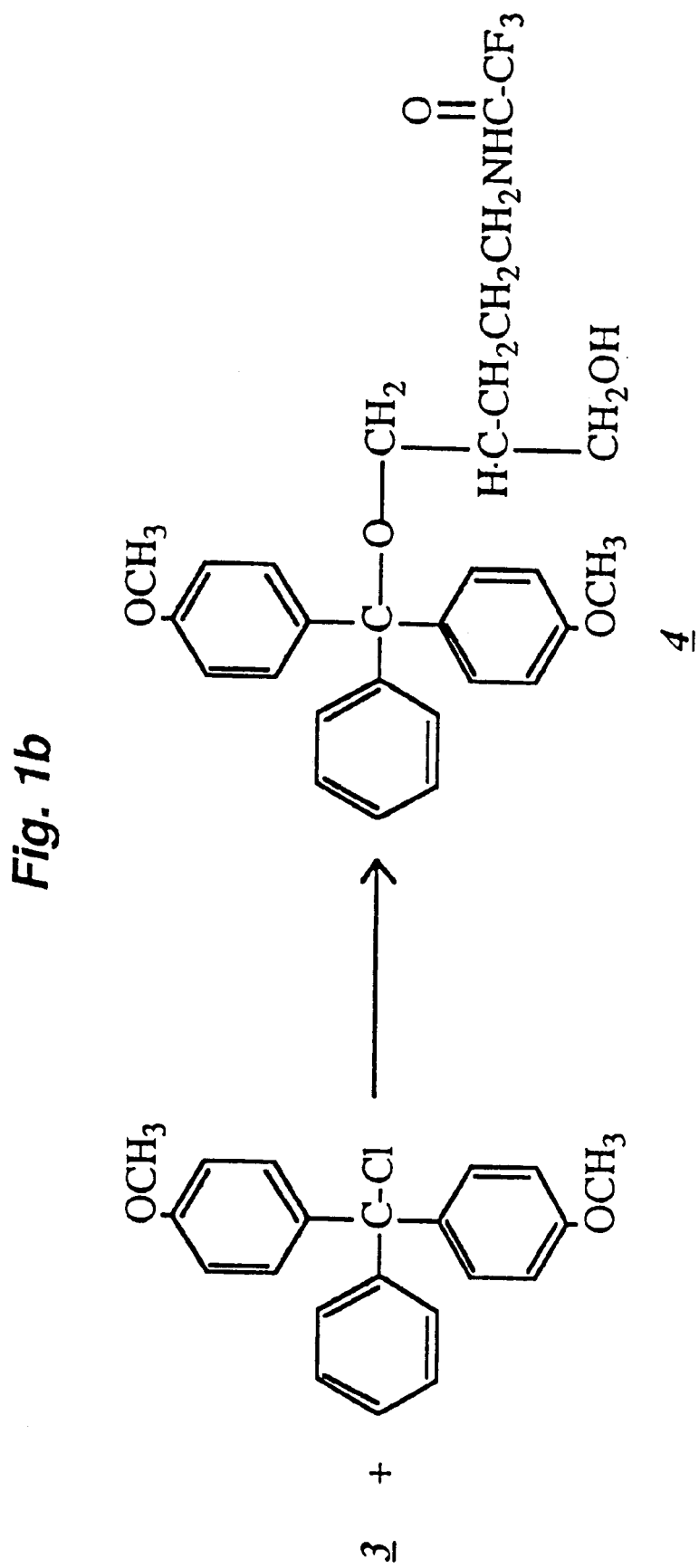
Figure 1C:
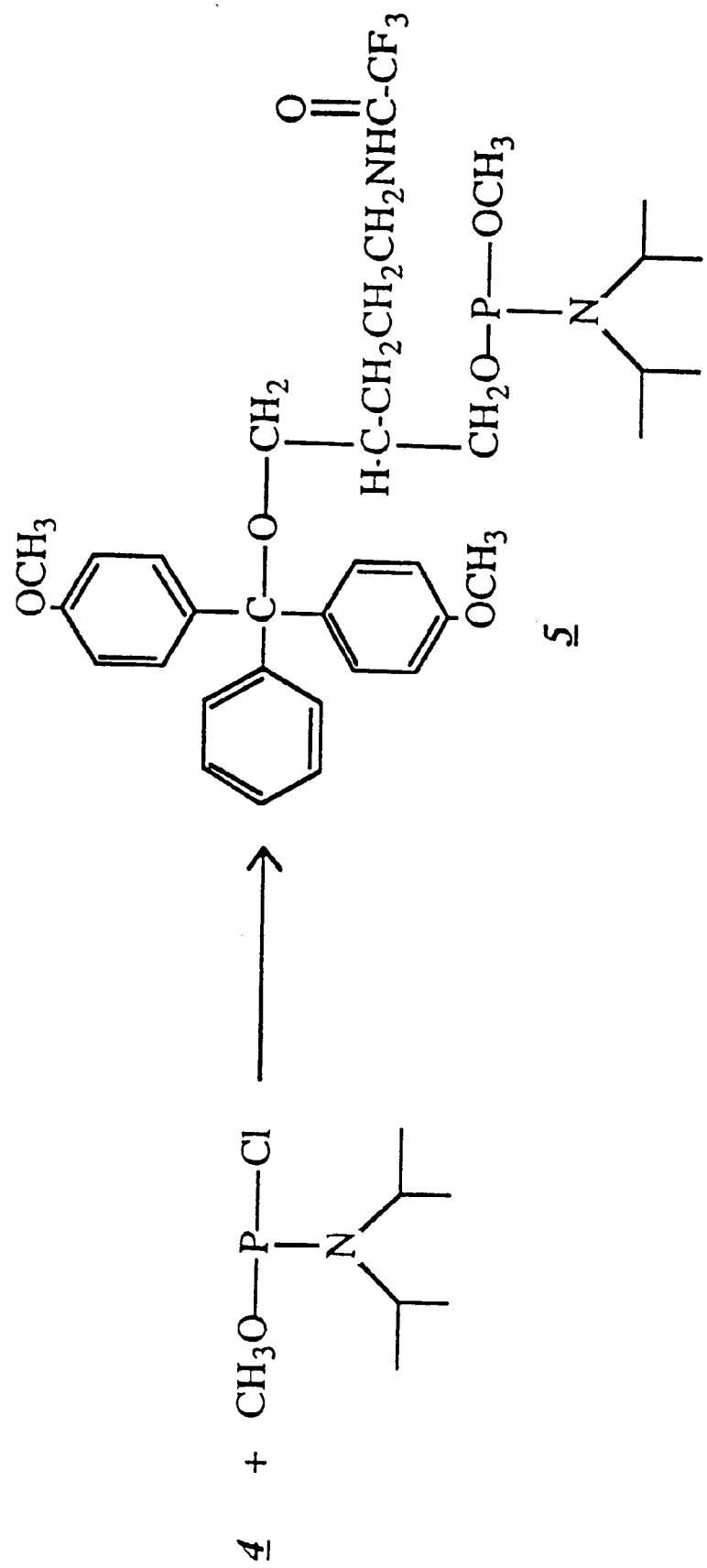

The synthetic scheme for this synthesis is given in FIG. 1, and is outlined below.

(a) Synthesis of 2-(Nitrilopropyl)-Diethyl Malonate (1)

The procedure used is an adaptation of the method of R. Adams and R. M. Kamm, organic Synthesis, Vol. 1 pp. 250–251, Gilman & Blatt, eds.

Materials: Diethyl malonate, 3-bromopropionitrile, and sodium ethoxide (21% solution in ethanol) were obtained from Aldrich Chemical Company (Milwaukee, Wis.). Absolute ethanol (200 proof) was from U.S. Industrial Chemicals.

Procedure: Sodium ethoxide (0.1) mole) was diluted with absolute ethanol to a final volume of 100 ml. A solution of diethyl malonate (0.1 mole) in a 50 ml of absolute ethanol was added dropwise with stirring, the reaction apparatus being protected from moisture with a CaCl2 drying tube. Stirring was continued for 1 hour at room temperature. A solution of 3-bromoproponitrile in 50 ml absolute ethanol was then added dropwise with stirring and the mixture was stirred overnight at room temperature. The resulting solution was filtered to remove precipitated sodium bromide, concentrated, and extracted into diethyl ether (50 ml). This solution was then extracted with water (50 ml), dried over anhydrous magnesium sulfate, and concentrated to an oil. Thin-layer chromatography on silica plates with chloroform as the mobil phase yielded three spots after visualization with iodine vapor: Rf 0.58, 0.51, and 0.38, which were subsequently identified as diethyl malonate, 2-(nitrilopropyl)-diethyl malonate, and 2,2-di-(nitrilopropyl) malonate, respectively. After several days in the refrigerator, crystals separated from the crude oil which were filtered off, dissolved in toluene (10 ml), and reprecipitated by addition of hexanes, giving 3.28 g white solid (12% yield); thin-layer chromatography (as described above), Rf 0.38. The structure of this compound was confirmed by $^1$H NMR (CDCl$_3$) to be 2,2-di-(nitrilopropyl) malonate (6): δ1.30 (t,6H), 2.26 (t, 4H), 2.47(t, 4H), 4.27 (q, 4H). The filtered oil was distilled under vacuum to give the title compound (1), (b.p. 99–103° C., 0.3 mm Hg) in 20% yield; $^1$H NMR analysis in CDCL3: δ1.24 (t, 6H), 2.19 (q, 2H), 2.47 (t, 2H), 3.46 (t, 1H), 4.18 (q, 4H).

(b) Synthesis of 2-(3-Aminopropyl)-1,3-Dihydroxypropane (2)

Materials: In addition to those listed in part (1), lithium aluminum hydride (1.0 M solution in diethyl ether) was purchased from Aldrich Fine Chemicals, Milwaukee, Wis.

Procedure: 2-(3-nitrilopropyl)-diethyl malonate (1, 3.21 g, 15.1 mmol) in anhydrous diethyl ether (50 ml) was added dropwise to a stirred solution of lithium aluminum hydride (0.1 mole in 100 ml diethyl ether) under nitrogen. The resulting mixture was refluxed for two hours and then stirred at room temperature overnight. Next, a 2.5 mM solution of sodium hydroxide in water (100 ml) was added slowly to quench unreacted hydride. This mixture was stirred for two hours, and the ether layer was decanted and discarded. (The product remains in the aqueous layer). The white gelatinous solid was removed from the aqueous layer by centrifugation, washed with water, and the aqueous supernatant and washings were combined and evaporated to a syrup under vacuum. Thin-layer chromatography (Analtech reverse-phase plates, water mobile phase, visualized with ninhydrin reagent) gave a major spot identified as the title compounds (2), Rf 0.48, and a minor spot attributed to a condensation side product, Rf. 0.29. The title compound (2) was purified by cation exchange chromatography (Dowex 50X8, 0.5 M HCl mobile phase) in an overall yield of 50%. $^1$H NMR analysis (D$_2$O): δ1.36 (apparent quartet, 2H), 1.68 (m, 3H), 2.97 (t, 2H), 3.57 (d, 4H).

(c) Synthesis of 2-(3-N-Trifluoroacetylaminopropyl)-1,3-Dihydroxpropane (3)

The procedure was adapted from the method of R. F. Goldfinger in Methods in Enzymology, Vol. XI, p. 317, incorporated herein by reference.

Materials: (In addition to those referenced supra.) S-Ethyl trifluorothioacetate was from Aldrich Fine Chemicals, Milwaukee, Wis.

Procedure: 2-(3-Aminopropyl)-1,3-dihydroxypropane (2), (3 mmol) was dissolved in water (25 ml). The pH of the solution was lowered to 9.5 by dropwise addition of 6 N HCl. The following reaction was performed in a hood: S-ethyl trifluorothioacetate (2 ml) was added dropwise to the vigorously stirring solution; the pH was maintained between 9.5 and 10.0 by dropwise addition of 6 N KOH. After thirty minutes, an additional milliliter of S-ethyl trifluorothioacetate was added, the pH being maintained as described above. The mixture was stirred for an additional forty-five minutes. Next, the pH was adjusted to 7 using 6 N KOH and the mixture was concentrated to dryness with rotary evaporation under vacuum. The residue was swirled with acetone (20 ml) and filtered to remove potassium acetate precipitate. The filtrate was concentrated to a syrup, redissolved in acetone (2 ml), and applied to a flash chromatography column containing forty grams of silica gel (40 um average particle diameter, from J. T. Baker Chemical Co. (Phillipsburg, N.J., U.S.A.). The column was eluted with a 50:50 solution (v/v) of methylene chloride/acetone (500 ml) taking 25 ml fractions. Fractions were analyzed for product content by spotting 2 ul aliquots onto silica gel plates, spraying with 10% piperidine in water, letting stand 15 minutes, drying with a heat gun, and then treating with ninhydrin reagent. Omission of the piperidine spray treatment prevented a calorimetric reaction with ninhydrin, confirming trifluoroacetylation of the primary amine. Using this procedure, product was found between fractions 13 and 18; these fractions were pooled and concentrated by rotary evaporation to give a colorless oil, Rf 0.4 (silica gel thin-layer chromatography using the same solvent system and method of visualization described above).

(d) Synthesis of 1-0-(Dimethoxytrityl)-2-(3-N-Trifluoroacetylaminopropyl-1,3-Dihydroxypropane (4)

Materials: (In addition to those listed supra). Dimethoxytrityl chloride was purchased from Aldrich Fine Chemicals (Milwaukee, Wis., U.S.A.). Methylene chloride was refluxed and distilled over CaH$_2$ and stored over 4 Angstrom (4 Å) molecular sieves. Pyridine was distilled over potassium hydroxide pellets and p-toluenesulfonate and stored under dry nitrogen.

Procedure: 2-(3-N-trifluoroacetylaminopropyl)-1,3-dihydroxypropane (3) (362 mg, 1.58 mmol) was dried with several evaporations of dry pyridine under reduced pressure and then further dried for several hours under full vacuum. The residue was then dissolved in 10 ml of dry pyridine under dry nitrogen. Dimethoxytrityl chloride (401 mg, 1.18 mmol) in dry methylene chloride (1.5 ml) was added with stirring, and the resulting solution was stirred for one hour at room temperature. The solvent was removed under reduced pressure and the residue was dissolved in chloroform (50 ml). This solution was extracted three times with 5% sodium bicarbonate in water and then was dried over anhydrous magnesium sulfate. The resulting solution was concentrated to an oil, redissolved in 2 ml of chloroform, and fractioned by flash chromatography as described supra except using chloroform/ethyl acetate/pyridine (95:5:0.2 v/v/v) as the mobile phase. Fractions were analyzed by thin-layer chromatography on silica plates using the same solvent system. Spots visualized with HCl fumes having Rf values of 0.27, 0.87 and 0.93, were identified as the 1-(dimethoxytrityl) product (4), dimethoxytritanol, and the 1,3-di-(dimethoxytrityl) side product, respectively. The latter material could be hydrolyzed to the title compound (4) by shaking with a mixture of 4% dichloroacetic acid in methylene chloride saturated with water. The product (4) was isolated by evaporation of the solvent from the appropriate fractions and dried under full vacuum, giving a foam (370 mg, 44%).

(e) Synthesis of 1-0-(Dimethoxytrityl)-2-(3-N-Trifluoroacetylaminopropyl)-3-0-(methyl-N,N-diisopropylphosphoramido)-1,3-Dihydroxypropane (5)

Materials: (In addition to those listed supra). N,N-Diisopropylethylamine and N,N-diisopropylmethylphosphoramidic chloride were purchased from Aldrich Chemical Company (Milwaukee, Wis., U.S.A). Dimethylformamide was refluxed and distilled over CaH and stored over 4 Å molecular sieves.

Procedure: 1-0-(Dimethoxytrityl)-2-(3-trifluoroacetylaminopropyl)-1,3-dihydroxypropane (4, 300 mg, 0.56 mmol) as dried with several evaporations of dry pyridine and dissolved in 10 ml of dry dimethylformamide. The following reaction was performed under dry nitrogen: N,N-diisopropylethylamine (245 ul, 1.3 mmol) was added with stirring, followed by N,N-diisopropylmethylphosphoramidic chloride (140 ul, 0.7 mmol). The reaction mixture was stirred for two hours. The mixture was then concentrated under reduced pressure and dissolved in methylene chloride (50 ml). This solution was extracted three times with 5% aqueous sodium bicarbonate, dried over anhydrous magnesium sulfate, and concentrated to an oil under reduced pressure. Conversion of the starting material (4) to the corresponding phosphoramidite (5) was confirmed by $^{31}$P NMR (CDCl$_3$, trimethyl phosphate, external standard): δ147.9. Purity was estimated at greater than 70%.

Figure 2A:
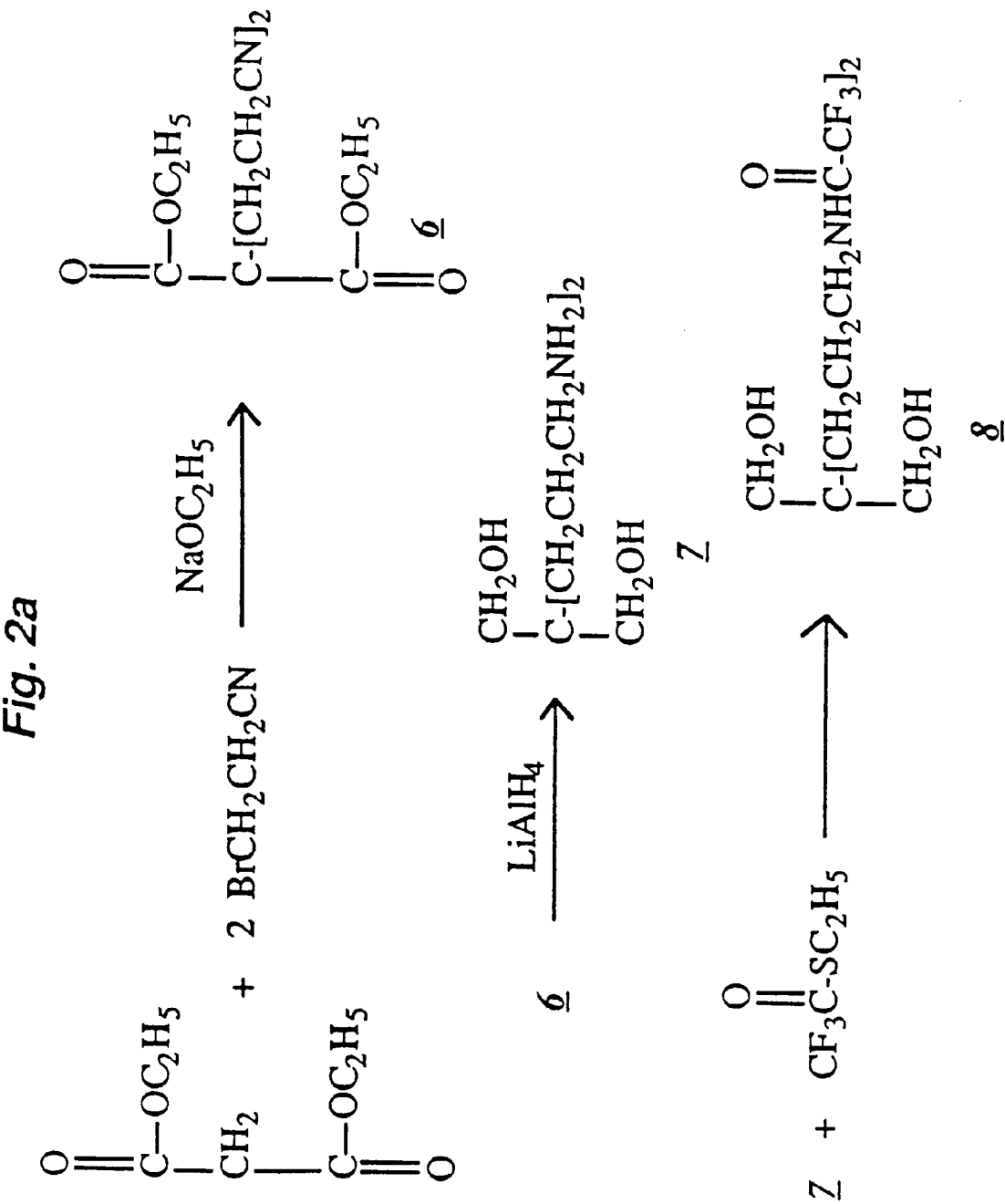
Figure 2C:
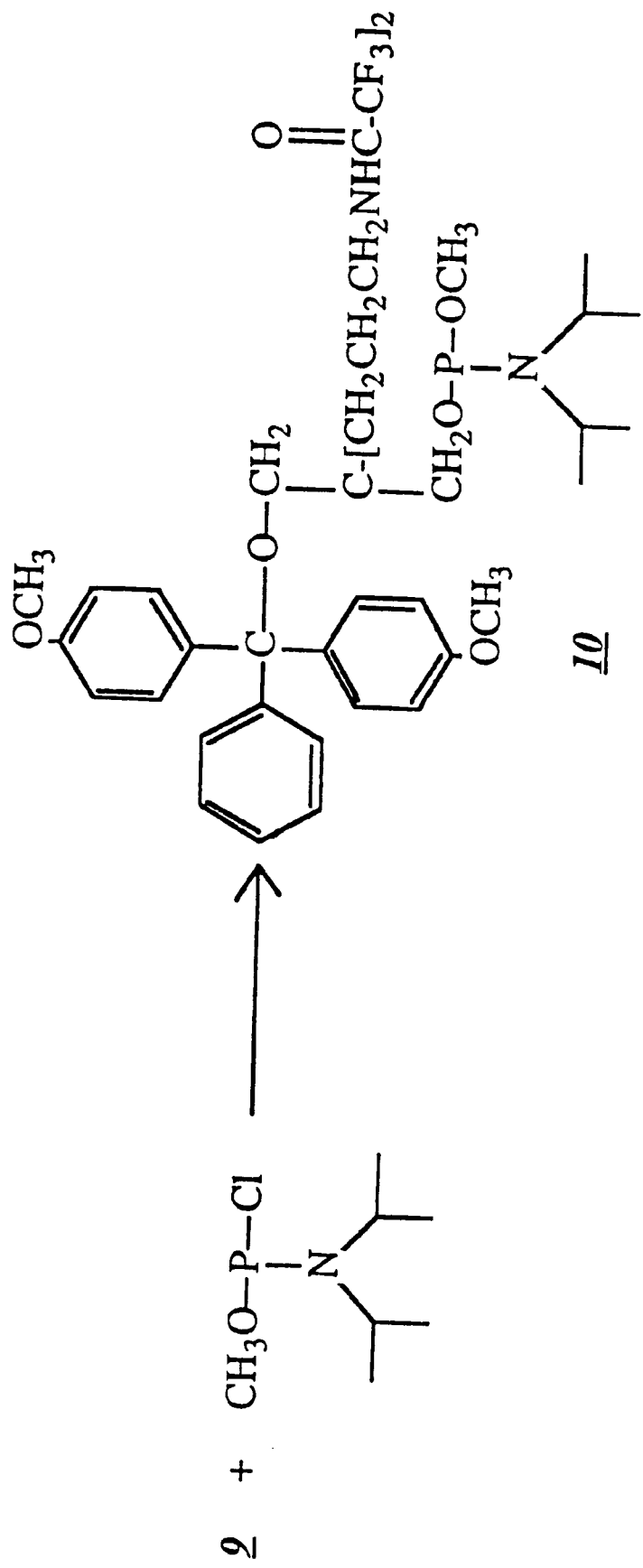

EXAMPLE 2
Synthesis of a 2,2-Di-(3-Aminopropyl)-1,3-Dihydroxypropane Linker Reagent This example consists of a monomer for incorporation into the phosphodiester skeleton of a synthetic oligonucleotide which possesses two aminopropyl linkers for multiple label attachment. The synthetic rationale is given in FIG. 2.

Materials: The materials are the same as those indicated in Example 1 except when specifically indicated.

(a) Synthesis of 2,2-Di-(3-Aminopropyl)-1,3-Dihydroxypropane (7)

The following procedure is a brief description of an adaptation of the method described supra in Example 1(b).

2,2-Di-(nitrilopropyl)-diethyl malonate (6) (2.00 g, 7.51 mmol), the synthesis of which has been described in Example 1(a), was dissolved in anhydrous diethyl ether (80 ml). The resulting solution was added dropwise to a stirred solution of lithium aluminum hydride (0.1 mole) in diethyl ether (100 ml). After fifteen minutes, the mixture was heated under reflux for two hours and then stirred at room temperature overnight. Work up and recovery of the crude product was performed as described supra in Example 1(b). Thin-layer chromatography, also as described in Example 1 (b), gave a major spot (Rf ca. 0.2).

(b) Synthesis of 2,2-Di-(3-Trifluoroacetylaminopropyl)-1,3-Dihydroxypropane (8)

2,2-Di-(3-aminopropyl)-1,3-dihydroxpropane (7) (3.7 mmol) was dissolved in water 25 ml) and the pH was adjusted to about 10 with 6 N HCl. 1.0 ml of S-ethyl trifluorothioacetate was added with vigorous stirring; the pH was maintained between 9.5 and 10.0 by dropwise addition of 6 N KOH. Two additional 1.0 ml additions of S-ethyl trifluorothioacetate were added likewise at thirty minute intervals. The mixture was concentrated to an oil under vacuum and then dissolved in acetone (30 ml). Precipitated potassium acetate was removed by filtration. The product (8) was purified by silica gel flash chromatography as described in Example 1(c) using methylene chloride/acetone (50:50 v/v) mobile phase. The purified material gave a single spot (Rf 0.7) with silica gel thin-layer chromatography using the same solvent system; visualization was by treatment with piperidine followed by ninhydrin as in Example 1(c). Yield was 510 mg (1.48 mmol).

(c) Synthesis of 1-0-(Dimethoxytrityl)-2,2-Di-(Trifluoroacetylaminopropyl)-1,3-Dihydroxypropane (9)

2,2-Di-(3-trifluoroacetylaminopropyl)-1,3-dihydroxypropane (8) (510 mg, 1.48 mmol) was dried with several evaporations of dry pyridine under vacuum and then dissolved in 5 ml of dry pyridine under nitrogen. Dimethoxytrityl chloride (376 mg, 1.11 mmol) in dry methylene chloride (1.5 ml) was added under nitrogen with stirring, and the mixture was stirred for one hour. The mixture was concentrated under reduced pressure and dissolved in chloroform (50 ml). This solution was extracted three times with saturated aqueous sodium bicarbonate and once with saturated sodium chloride. The solution was then dried over anhydrous magnesium sulfate, and concentrated to an oil under vacuum. Next, the oil was dissolved in 2 ml of chloroform and fractionated by silica gel flash chromatography as described above using chloroform/ethyl acetate/pyridine (80:20:0.2 v/v/v). The product (9) was identified by silica gel thin-layer chromatography using the same solvent system, visualizing with HCl fumes (Rf 0.3); it was concentrated under reduced pressure and dried under full vacuum to give a pale yellow foam (517 mg, 52%).

(d) Synthesis of 1-0-(Dimethoxytrityl)-2,2-Di-(3-Trifluoroacetylaminopropyl)-3-0-(Methyl-N,N-Diisopropylphosphoramido)-1,3-Dihydroxypropane (10)

Procedure: 1-0-(Dimethoxytrityl)-2,2-di-(trifluoroacetylaminopropyl)-1,3-dihydroxypropane (9) (136 mg, 0.2 mmol) was dried with three co-evaporations of dry pyridine (3 ml). The resulting residue was dissolved in dry methylene chloride (1.5 ml) under argon and N,N-diispropylethylamine (175 ul, 1.0 mmol) was added with stirring. Next, N,N-diisopropylmethylphosphoramidic chloride (80 ul, 0.4 mmol) was added, and the reaction was stirred for 1 hour. The resulting mixture was diluted with ethyl acetate/triethylamine (98.2) (50 ml) and extracted twice with saturated aqueous sodium bicarbonate (25 ml). The organic layer was dried over anhydrous MgSO$_4$ and concentrated to an oil (240 mg). Conversion to the phosphoramidite (10) was confirmed by $^{31}$P NMR (CDCl$_3$ trimethoxy phosphate, external standard): δ145.5. Purity was estimated at greater than 60%.

EXAMPLE 3
Synthesis of a 3-Amino-1,2-Propanediol Based Linker Reagent

Figure 3A:
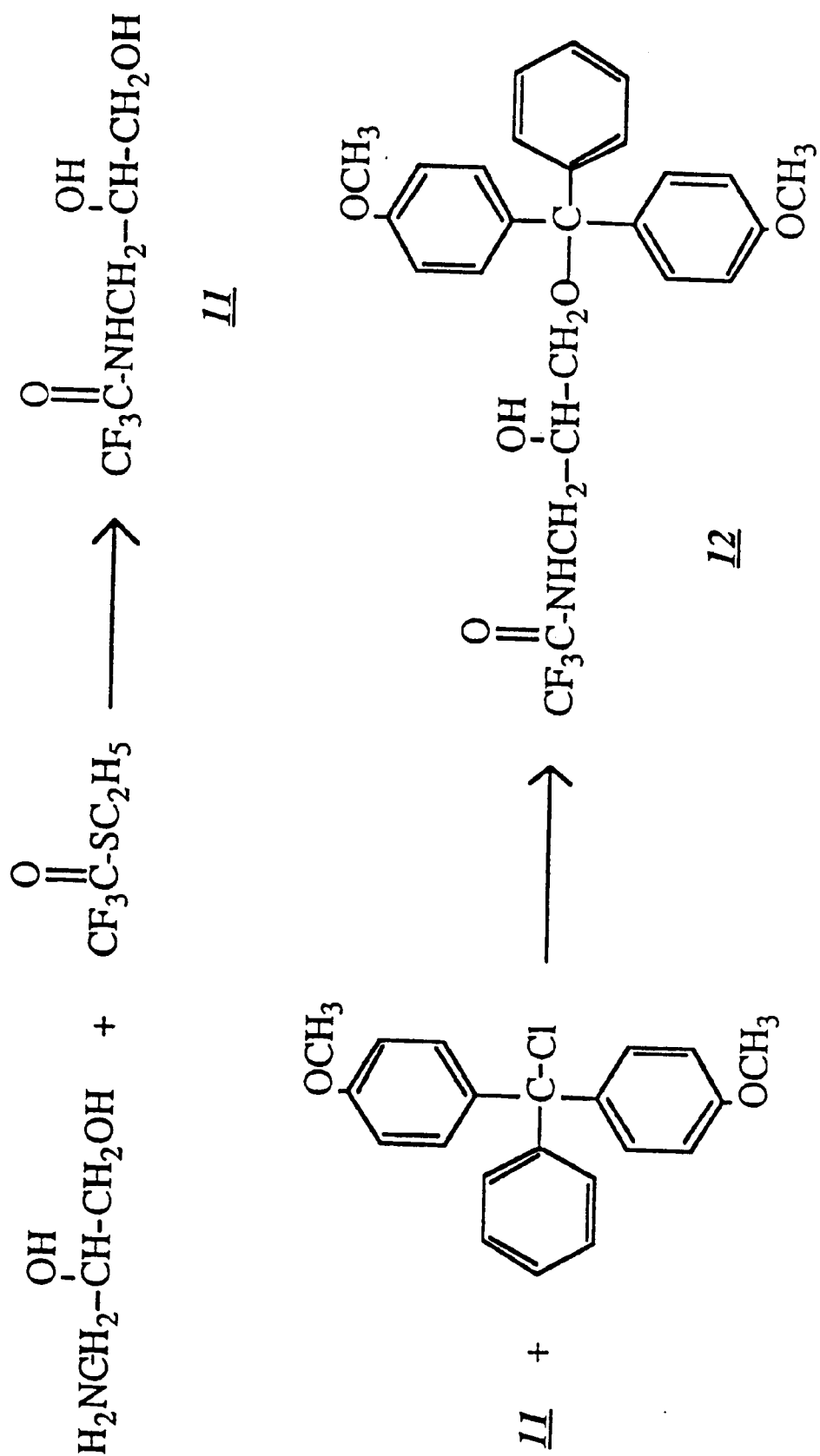
FIGS. 3a and 3b illustrate the preparation of still another reagent of the present invention.
Figure 3B:
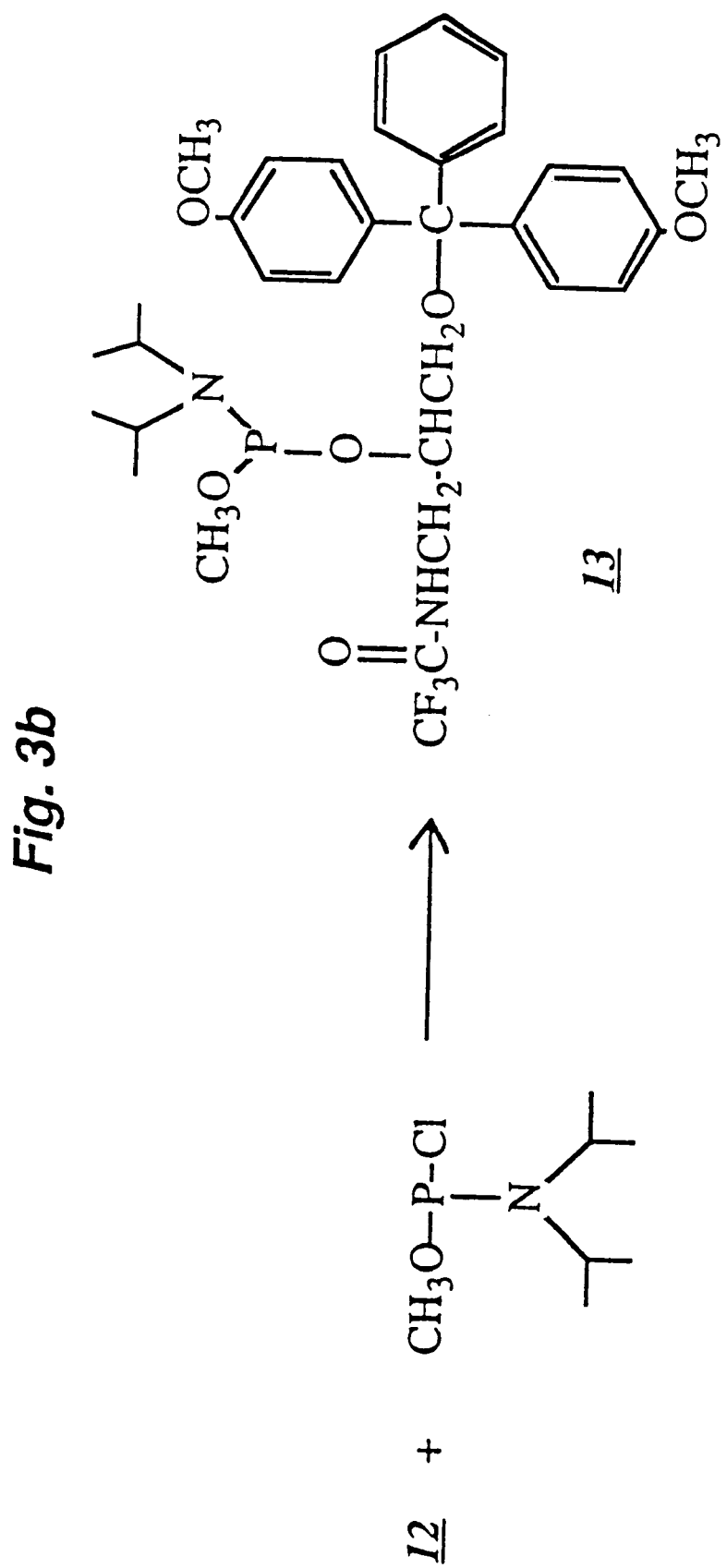
Figure 4A:
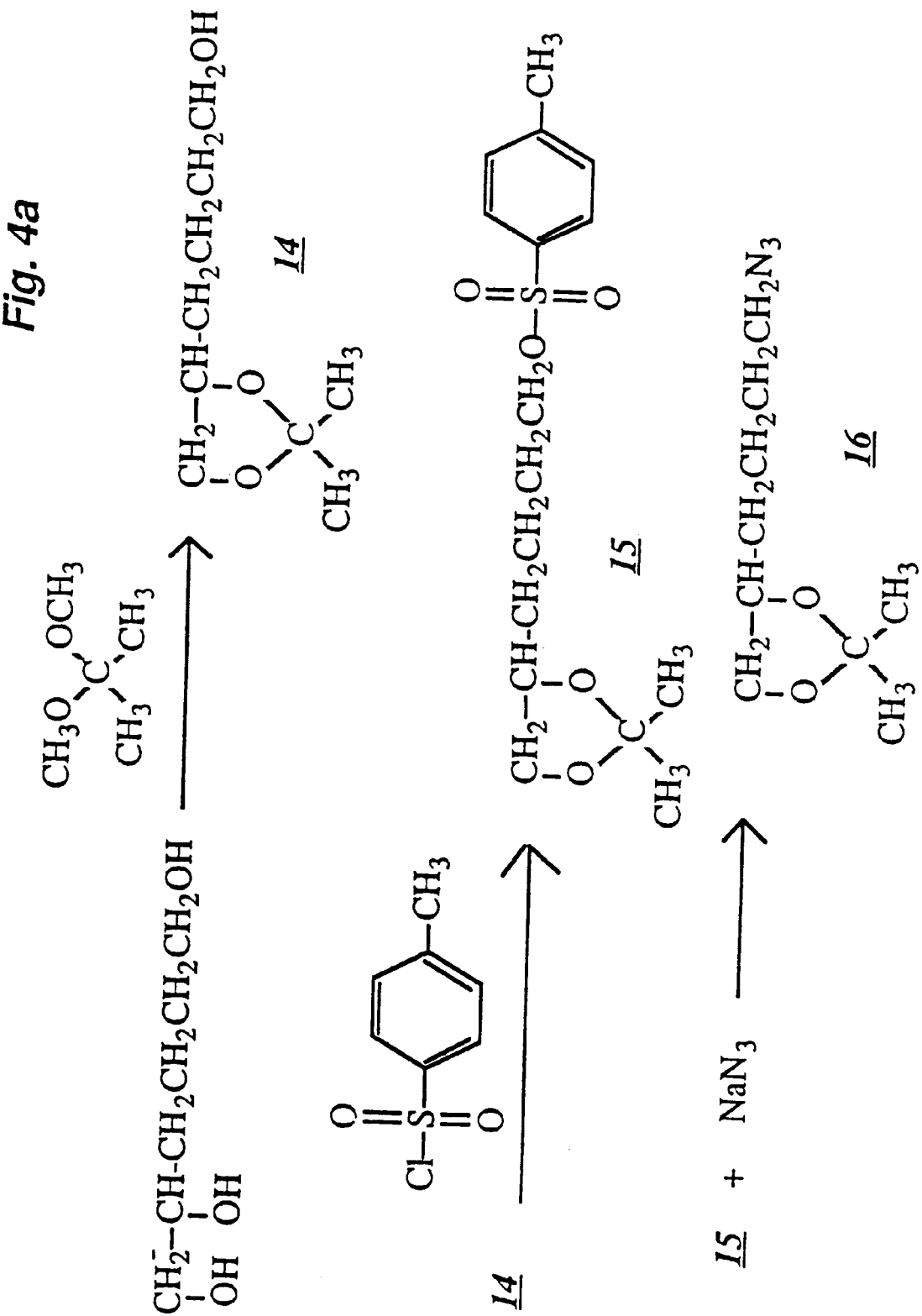
FIGS. 4a to 8b illustrate the preparation of still other reagents of the present invention.
Figure 4B:
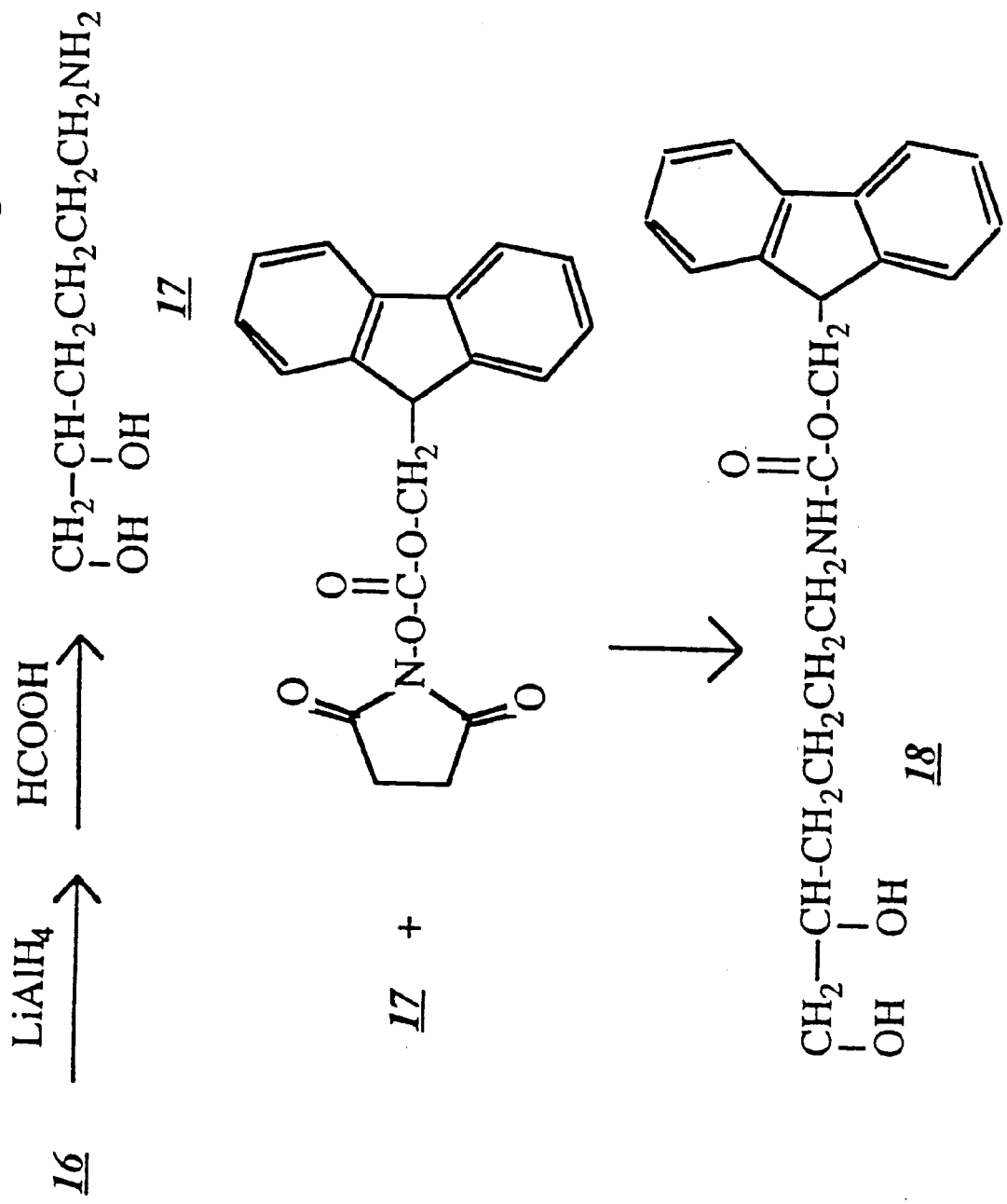
Figure 4C:
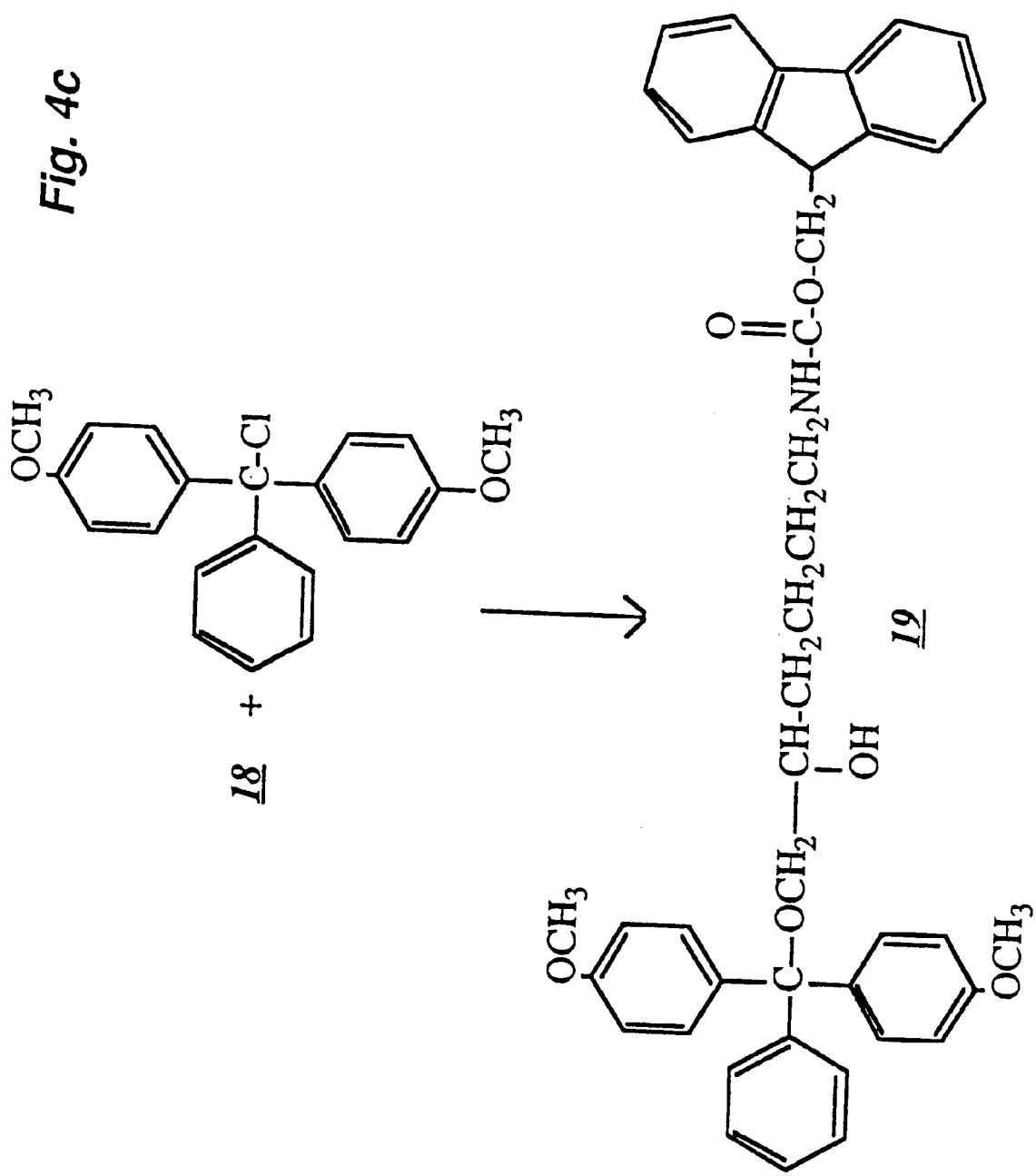
Figure 4D:
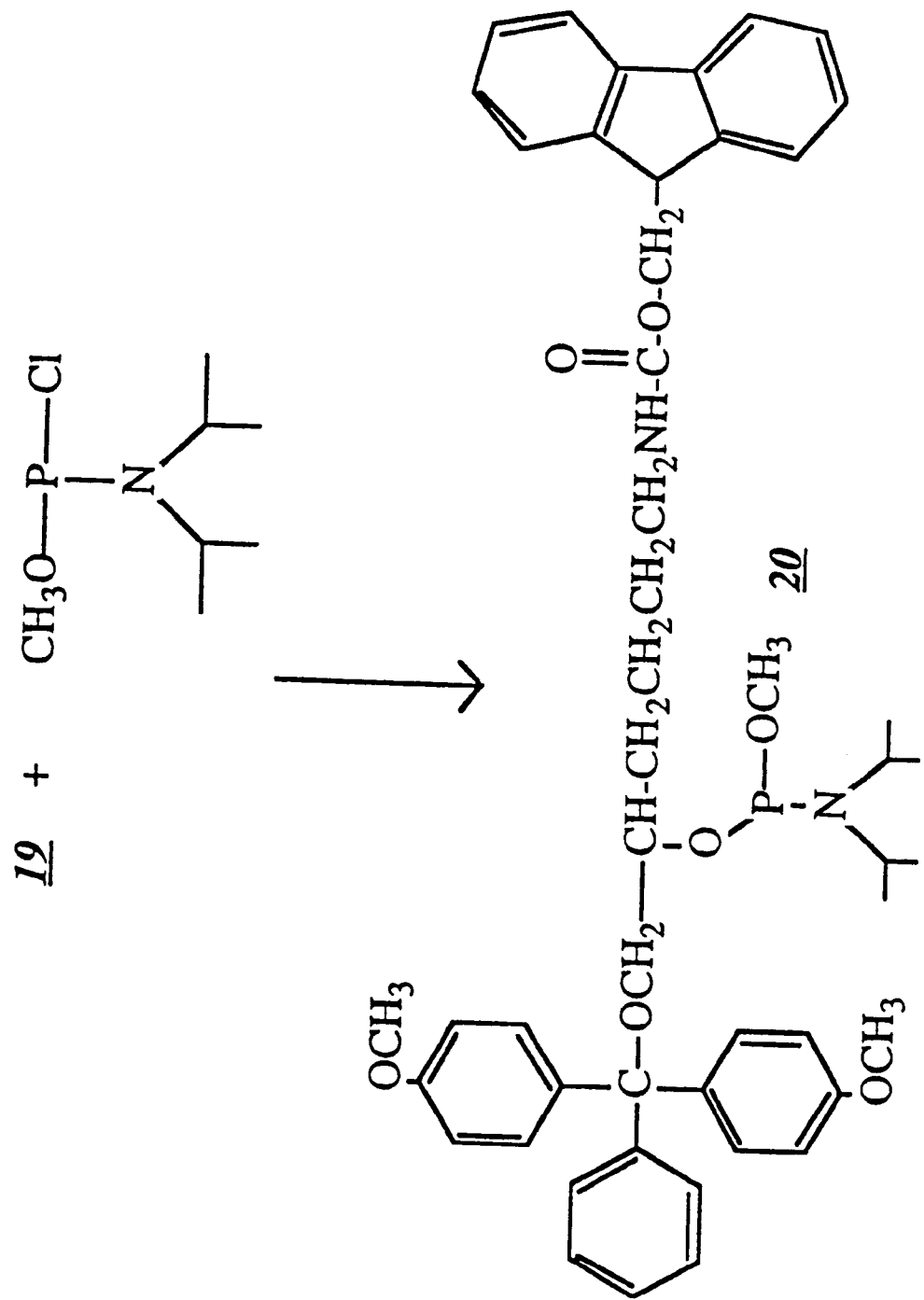

The synthesis is diagrammed in FIG. 3, and is described below.

(a) Synthesis of a 3-(Trifluoroacetylamino)-1,2-Propanediol (11)

Materials: 3-Amino-1,2-propanediol and S-ethyl trifluorothioacetate were purchased from Aldrich Chemical Co. (Milwaukee, Wis., U.S.A.).

Procedure: S-Ethyl trifluorothioacetate (5.13 ml, 45 mmol) was added to a rapidly stirring mixture of 3-amino-1,2-propanediol (2.32 ml, 30 mmol) and ethyl acetate (5.0 ml). After several minutes, the mixture became homogeneous. After one hour, the reaction solution was shaken with petroleum either (100 ml), giving an oil which was separated and concentrated under vacuum. This material was analyzed by thin-layer chromatography on silica plates using ethyl acetate/methylene chloride (2.1) as the mobile phase. The plates were visualized first with ninhydrin reagent, which revealed a trade of unreacted amine starting material at the origin. Next, the plates were visualized by spraying with 10% aqueous piperidine, drying with a heat gun after 15 minutes, and then treating with ninhydrin reagent. In the latter case, a major spot was apparent (Rf 0.28) which was estimated to comprise greater than 95% of the material. Purification of the material associated with the major spot (11) was achieved by preparative-scale thin-layer chromatography.

(b) Synthesis of 3-(Trifluoroacetylamino)-1-0-(Dimethoxytrityl)-1,2-Propanediol (12)

The materials and general procedure are described supra in Example 1(d).

3-(Trifluoroacetylamino)-1,2-dihydroxypropane (11) (1.87 g, 10 mmol) was dried by three co-evaporations of dry pyridine (10 ml) under reduced pressure. The material was then dissolved in dry pyridine (10 ml). Next, a solution of dimethoxytrityl chloride (3.73 g, 11 mmol) in dry pyridine (10 ml) was added dropwise with stirring under nitrogen. After ca. one hour, methanol (0.2 ml) was added. The resulting solution was diluted with ethyl acetate (80 ml) and extracted twice with saturated aqueous sodium bicarbonate (30 ml) and twice with water (20 ml). The organic layer was dried over anhydrous magnesium sulfate and concentrated under reduced pressure to give 6 grams of crude oil. 1.1 grams of the crude material was fractionated by silica gel flash chromatography as described above using methylene chloride/ethyl acetate/pyridine (10:1:0.01 v/v/v). Fractions were analyzed by thin-layer chromatography on silica gel plates with the same solvent system. Spots were visualized with HCl fumes, revealing two minor components at Rf values of 0.94 and 0.87 and a major component at Rf 0.53 which were identified as the 1,2-di-(dimethoxytrityl) side product, dimethoxytritanol, and the predicted product (12), respectively. Fractions having an Rf of 0.53 by thin-layer chromatography as described above, were pooled and evaporated to give 0.72 g of (12), the structure of which was confirmed by $^1$H NMR. The overall yield of (12) was 80% based on the yield form the flash column.

(c) Synthesis of 3-(Trifluoroacetylamino)-1-0-(Dimethoxytrityl)-2-0-(methyl-N,N-diisopropylphosphoramido)-1,2-Propanediol (13)

The reagents for this synthesis are given supra in Example 1.

3-(Trifluoroacetylamino)-1-0-(dimethoxytrityl-1,2-propanediol (12) (196 mg, 0.4 mmol) was dissolved in dry methylene chloride (1.5 ml) containing diisopropylethylamine (348 ul, 2 mmol). N,N-diisopropylmethylphosphoramidic chloride (200 ul, 1 mmol) was added dropwise with stirring under argon. After one hour, ethyl acetate containing 1% triethylamine was added (50 ml), and the resulting solution was extracted three times with saturated aqueous sodium bicarbonate. The organic layer was dried over anhydrous magnesium sulfate and concentrated to an oil under reduced pressure. The purity of this material was estimated to be greater than 95% by $^{31}$P NMR (CD$_3$CN, trimethoxy phosphoric acid, external standard): δ147.5. Attempts to crystallize this material in toluene/hexane mixtures at −78° C. were unsuccessful; the crude sample was therefore used directly for linker addition.

EXAMPLE 3(A)

Synthesis of 6-Amino-1,2-Hexanediol Based Linker Reagent

The synthesis is diagrammed in FIG. 4, and is described below.

(a) Synthesis of 1,2-(Isopropylidine)-1,2,6-trihydroxyhexane (14)

Materials: 1,2,6-Trihydroxyhexane and 2,2-dimethoxypropane were purchased from Aldrich Chemical Co. (Milwaukee, Wis., U.S.A.).

Procedure: 1,2,6-trihydroxyhexane (1.00 g, 7.45 mmol), dry acetone (10 ml) and concentrated sulfuric acid (30 ul) were added to a 50 ml round bottom slash along with a magnetic stir bar. The flask was purged with nitrogen and a rubber septum was attached to exclude moisture. Next, 2,2-dimethoxypropane (3.00 ml, 24.4 mmol) was added slowly by syringe to the stirring solution over a 30 minute time period. Stirring was continued for 2 hours. Anhydrous sodium carbonate (150 mg) as added to quench the reaction, and the contents were then stirred overnight. Finally, the solution was filtered and concentrated under vacuum to give a pale yellow syrup (1.6 g). This material was used in the next step without purification.

(b) Synthesis of 1,2-(Isopropylidine)-6-(p-toluenesulfonyl)-1,2,6-trihydroxyhexane (15)

Materials: p-Toluenesulfonyl chloride was purchased from Aldrich Chemical Co. (Milwaukee, Wis., U.S.A.).

Procedure: The crude isopropylidinated material from the previous step (14, approx. 7.45 mmol) was dissolved in dry acetone (15 ml). Next, p-toluenesulfonyl chloride (2.8 g, 14.9 mmol) and dry pyridine (5 ml) were added, and the contents were stirred for 3 hours at room temperature with exclusion of moisture. The solvent was then removed under vacuum and the residue was partitioned between methylene chloride (25 ml), dried over anhydrous magnesium sulfate, filtered, and then concentrated under vacuum to give a crystalline solid (15, 2.8 g). The crude product was purified by silica gel flash chromatography as described above using chloroform as the mobile phase. Fractions were analyzed by thin-layer chromatography on fluorescent silica gel plates using the same solvent. Spots were visualized under an ultraviolet lamp. Fractions containing product (R$_f$ 0.50) were pooled and concentrated under vacuum to give an oil (15, 2.37 g) in 96.9% overall yield.

(c) Synthesis of 1,2-(Isopropylidine)-6-Azido-1,2-Dihydroxyhexane (16)

Procedure: The tosylate from the previous step (15, 2.37 g, 7.22 mmol) was dissolved in dry dimethylformamide (30 ml). Sodium azide (1.64 g, 25.2 mmol) was added along with a magnetic stir bar, and a reflux condenser and CaCl$_2$ drying tube were attached. The mixture was then stirred in a water bath at 60–65 degrees C. for 3 hours. Stirring was continued overnight at room temperature. The precipitate was then removed by centrifugation, and the resulting solution was concentrated under vacuum to a final volume of approximately 5 ml. The concentrated solution was partitioned between chloroform (50 ml) and water (15 ml). The organic layer was further washed with water (15 ml), dried over anhydrous MgSO, filtered, and concentrated under vacuum to an amber oil (16). The crude product was then used in the next step without further purification.

(d) Synthesis of 6-Amino-1,2-Dihydroxyhexane (17)

Materials: A solution of lithium aluminum hydride (1.0 M) in diethyl ether was purchased from Aldrich Chemical Company (Milwaukee, Wis., U.S.A).

Procedure: Anhydrous diethyl ether (10 ml) and a solution of lithium aluminum hydride (1.0 M) in diethyl ether (15 ml) were added to a 250 ml round bottom flask under an argon atmosphere. A solution of the crude azide from the previous step (16, ca. 7 mmol) in anhydrous diethyl ether (25 ml) was then added through an addition funnel with stirring under argon. Following complete addition, the mixture was stirred under argon. Following complete addition, the mixture was stirred under reflux for 90 minutes. The resulting slurry was diluted with diethyl ether (25 ml), and the following solutions were added with stirring in the order indicated: water (1 ml), 5 N NaOH (1 ml) and water (1 ml). The mixture was then filtered through a medium glass scinter. The filtrate was concentrated by distillation at room temperature followed by high vacuum to give a pale yellow oil. Next, water (10.8 ml) and 88% formic acid (14.2 ml) were added. The resulting mixture was left overnight at room temperature and then heated at 70–75 degrees C. for 2 hours. The solution was concentrated under vacuum to a syrup, which was then dissolved in water (50 ml) and applied to a cation exchange column containing AG 50W-X8 resin (H form, 50 ml bed volume, Bio-Rad Labs, Richmond, Calif., U.S.A). The column was eluted with 1 N HCl. Fractions containing the amine product were visualized by spotting onto silica gel TLC plates, spraying with ninhydrin reagent, and heating as described above. Fractions containing product were pooled and concentrated under vacuum to give a syrup, which was further co-evaporated with methanol to give pale yellow needles (17, as the hydrochloride).

(e) Synthesis of 6-N-(9-Fluorenylmethoxycarbonyl)-Amino-1,2-Dihydroxypropane (18)

Materials: 9-Fluorenylmethylsuccinimidyl carbonate (Fmoc-NHS) was purchased from Bachem, Inc. (Torrance, Calif. U.S.A).

Procedure: 6-amino-1,2,-dihydroxyhexane hydrochloride (17), in an amount according to the yield obtained in the previous step, was dissolved in water (10 ml) and adjusted with 5 N NaOH to a final pH of 8.7. Sodium bicarbonate (588 mg, 7 mmol), Fmoc-NHS (2.76 g, 7 mmol) and acetone (10 ml) were added. The suspension was stirred overnight at room temperature, after which time all of the Fmoc-NHS had gone into solution. The reaction mixture was concentrated under vacuum to remove acetone. 1 N HCl (50 ml) and ethyl acetate (150 ml) were added, and the mixture was transferred to a separatory funnel. The organic layer was separated and washed with 0.1 N HCl (50 ml) followed by water (2×50 ml). Next, the organic layer was dried over anhydrous $MgSO_4$, filtered, and concentrated to an oil. The product was purified by silica gel flash chromatography as described above using chloroform/acetone (50:50) as the mobile phase. Fractions were analyzed by thin-layer chromatography on fluorescent silica gel plates using the same solvent system. Spots were visualized under an ultraviolet lamp. Fractions containing product ($R_f$ 0.25) were pooled and evaporated to give a white crystalline solid (18, 1.20 g). The overall yield was 45%, based on the amount of 1,2,6-trihydroxyhexane starting material.

(f) Synthesis of 1-0-(Dimethoxytrityl)-6-N-(Fluorenylmethoxycarbonyl)-6-Amino-1,2-Dihydroxyhexane Procedure: The product from the previous step (18, 0.5 g, 1.41 mmols) was co-evaporated with dry pyridine (3×3 ml) and then dissolved in dry pyridine (8 ml) under argon. A solution of dimethoxytrityl chloride (0.5736 g, 1.69 mmols) in dry methylene chloride (2 ml) was added by syringe with stirring over a period of several minutes. Stirring was continued for 2 hours at room temperature, after which methanol (100 ul) was added to quench the reaction. The solvent was removed under vacuum and the residue was dissolved in chloroform (100 ml). The resulting solution was transferred to a separatory funnel and washed with saturated aqueous sodium bicarbonate (3×20 ml) followed by 5 M NaCl (20 ml). The organic layer was then dried over anhydrous $MgSO_4$, filtered, and concentrated to an oil under vacuum. The product was purified by silica gel flash chromatography as described above using a methylene chloride/ethyl acetate/triethylamine (95:5:0.5) solvent system. Fractions were analyzed by thin-layer chromatography on silica gel plates using the same solvent; spots were visualized by subjecting the plates to HCl fumes. Fractions containing product (19, $R_f$ 0.35) were pooled and evaporated under vacuum to a foam (910 mg, 100% of the theoretical yield).

(g) Synthesis of 1-0-(Dimethoxytrityl)-6-N-(Fluorenylmethoxycarbonyl)-2-0-(Methyl-N,N-Diisopropylphosphoramido)-6-Amino-1,2-Dihydroxyhexanes (20)

Materials: The materials are described in the preceding examples, supra.

Procedure: N,N-diisopropyl-methoxyphosphinyl chloride (102 ul, 0.513 mmol) was added dropwise to a stirring solution of 19 (225 mg, 0.34 mmol) and N,N-diisopropyl ethylamine (236 ul, 1.36 mmol) in dry methylene chloride (3 ml) under an argon atmosphere. After 90 minutes, the reaction mixture was diluted into ethyl acetate containing 2% triethylamine (50 ml) and washed with saturated aqueous sodium bicarbonate (2×25 ml). The organic layer was dried over anhydrous $MgSO_4$, filtered, and evaporated to dryness under vacuum. The residue was dissolved in toluene (2 ml) and added dropwise with rapid stirring to petroleum ether at −20 degrees C. The resulting mixture was then stored at −20 degrees C. for 16 hours. It was then warmed to room temperature and the supernate was decanted. The precipitated product (20) was then dried under vacuum: yield =160 mg (58% yield). The purity of this material was demonstrated by thin-layer chromatography on silica gel plates using a methylene chloride/ethyl acetate/triethylamine (10:1:0.1) solvent system and visualization under ultraviolet light ($R_f$ 0.9, compared with an $R_f$ of 0.25 for the starting material).

Figure 5A:
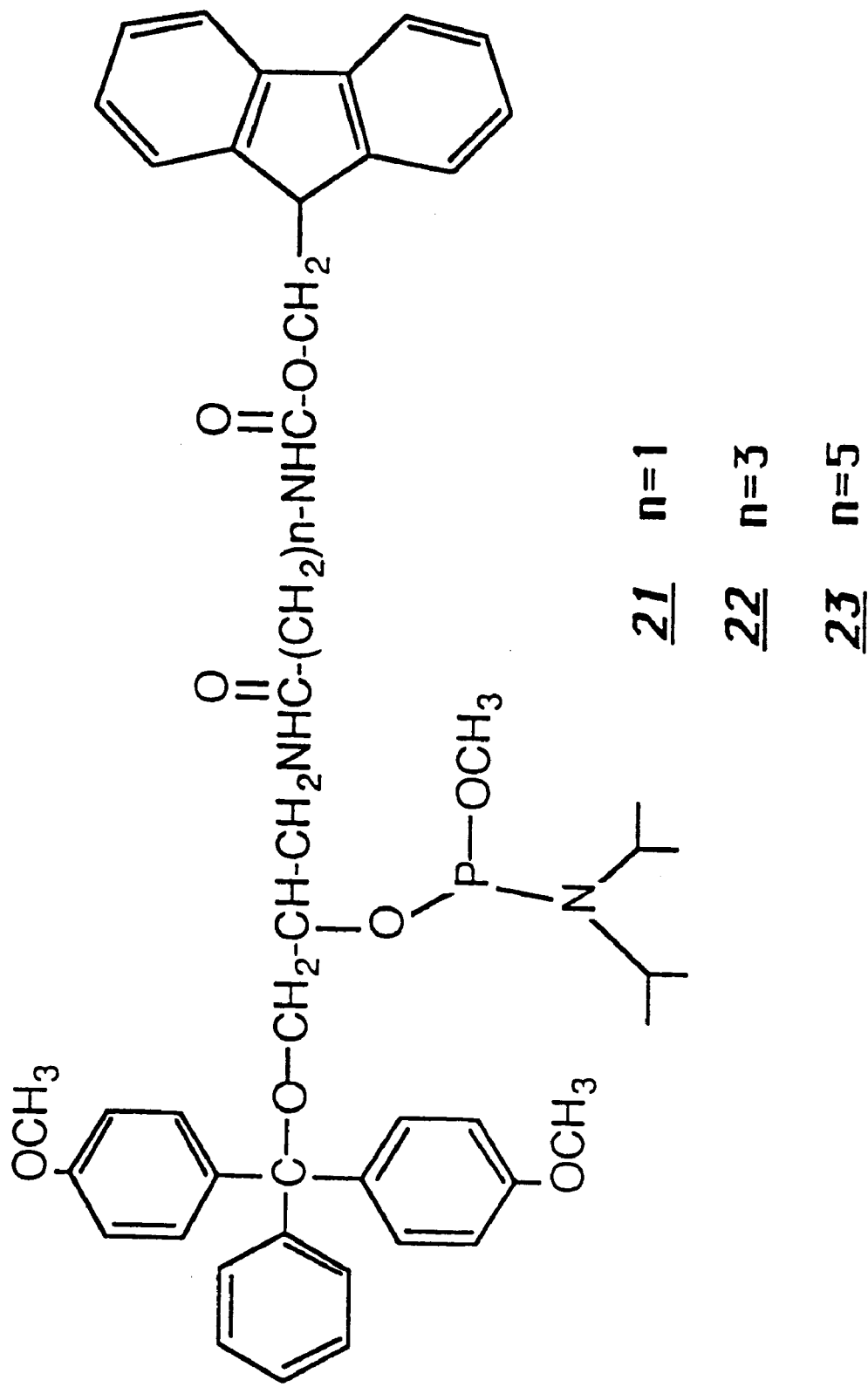
Figure 5B:
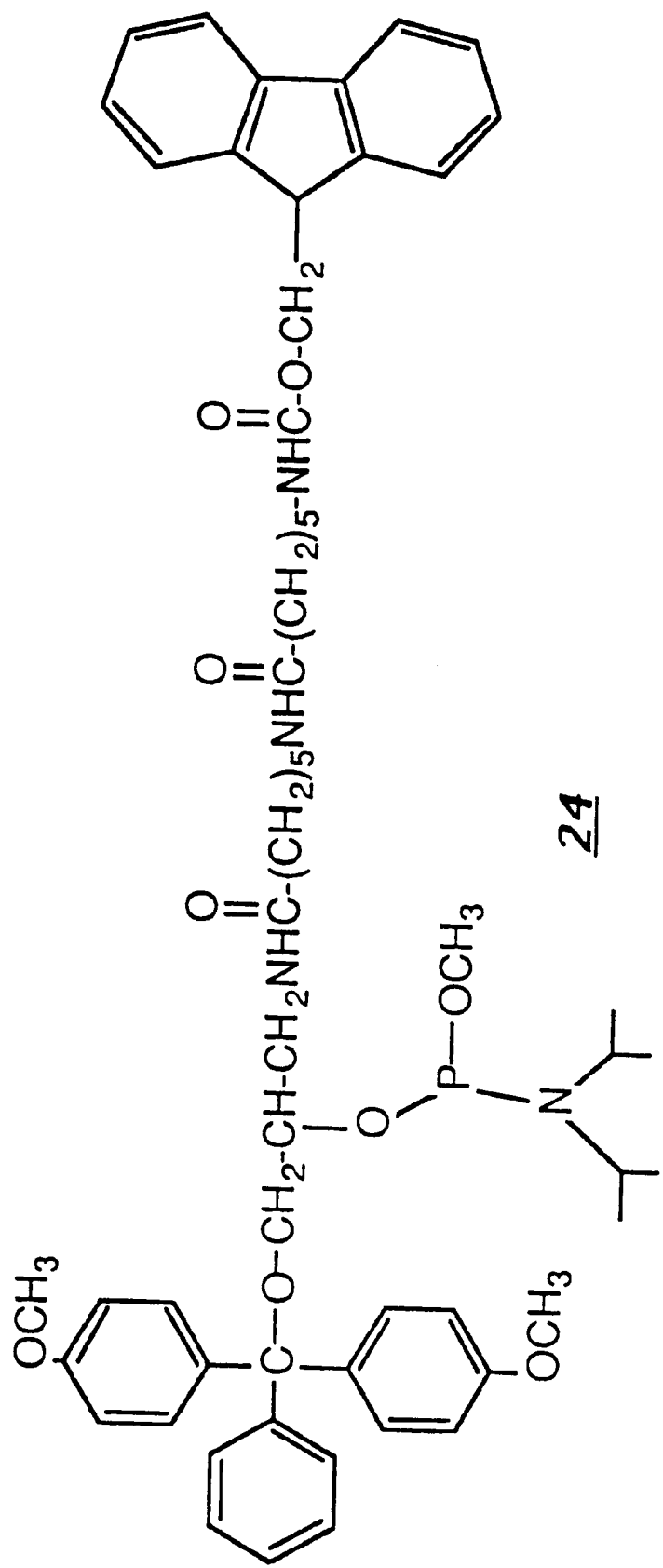

Extended analogs of the linker reagent described in Example 3(A), supra, were also generated. The structure of these analogs are illustrated in FIG. 5 (21–24). The preparation of these analogs is described in the following examples.

EXAMPLE 3(B)

Synthesis of a 3-N-(glycidyl)-Amino-1,2-Propanediol Based Linker Reagent (21)

Figure 6A:
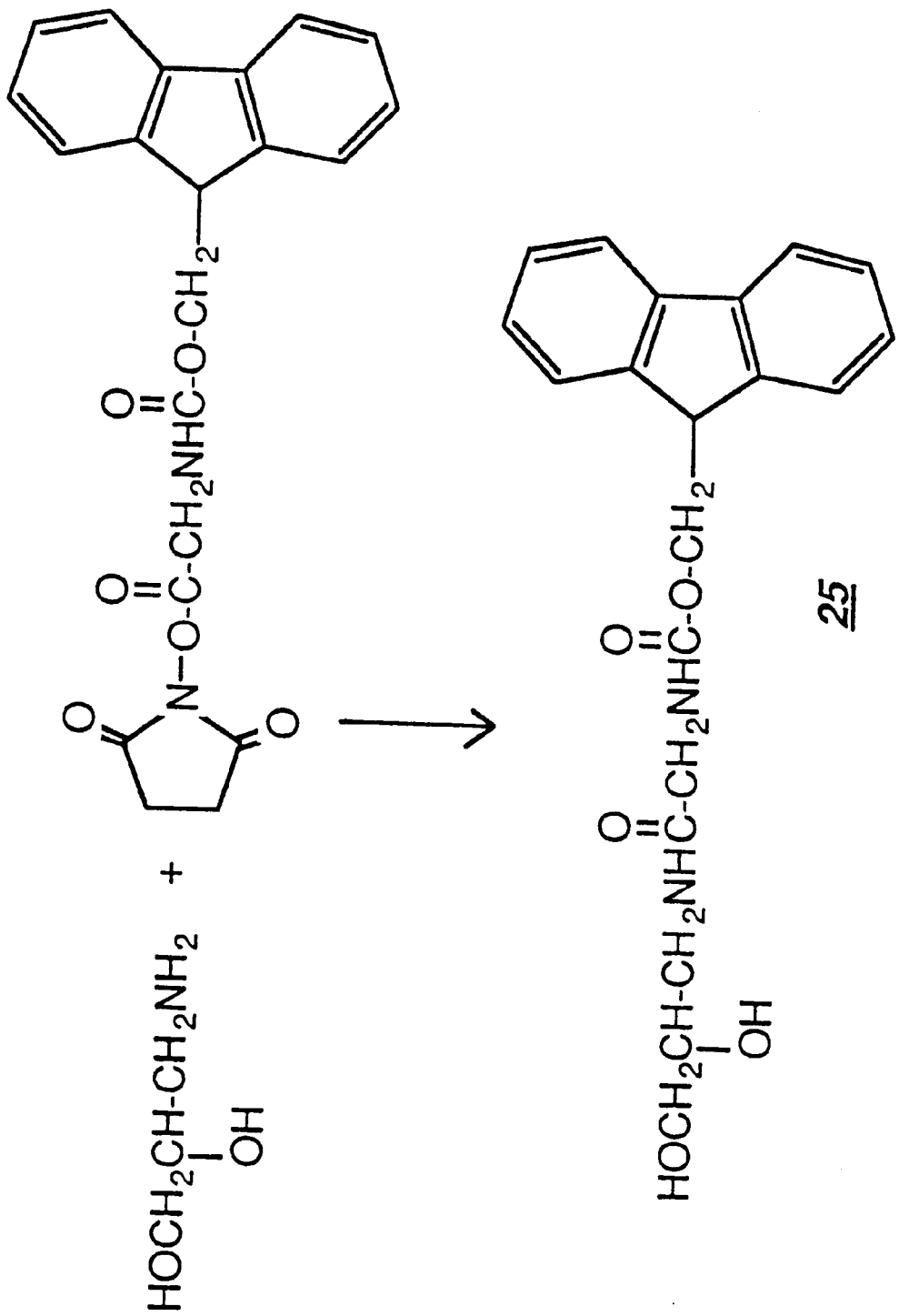
Figure 6B:
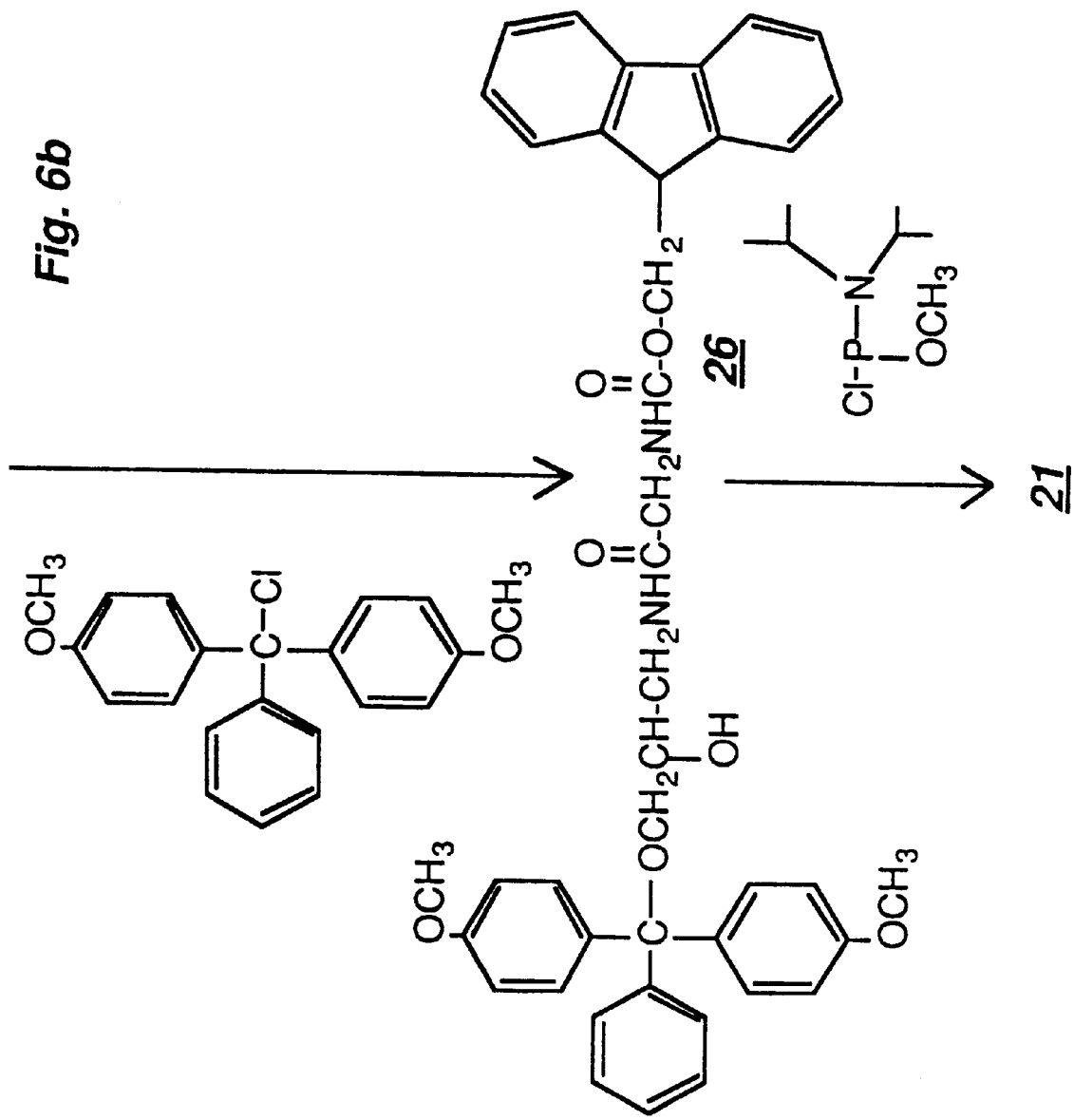

The scheme for this synthesis is outlined in FIG. 6.

(a) Synthesis of 3-N-[N-(Fluorenylmethoxycarbonyl)-glycidyl]-amino-1,2-propanediol (25)

Materials: N-(Fluorenylmethoxycarbonyl)-glycine-N-Hydroxysuccinimide (Fmoc-glycine-NHS) was purchased from Bachem, Inc. (Torrance, Calif., U.S.A). Other reagents have been described supra.

Procedure: 3-Amino-1,2-propanediol (91 mg, 1 mmol) was added to a solution of Fmoc-glycine-NHS (394 mg, 1 mmol) in acetone (7 ml). To this solution was added a solution of sodium bicarbonate (84 mg, 1 mmol) in water (5 ml). The reaction mixture was stirred at room temperature for 16 hours. Thin-layer chromatography using silica gel plates and a methylene chloride/methanol/acetic acid (20:2:0.1) solvent system revealed that the reaction had gone to completion. The product (25) appeared in the flask as a precipitate, which was filtered off and dried under vacuum over $P_2O_5$ for two days. The yield was 310 mg (84%).

(b) Synthesis of 1-0-(Dimethoxytrityl)-3-N-[N-(Fluorenylmethoxycarbonyl)-glycidyl]-Amino-1,2-Propanediol (26)

Materials: The materials are described in preceding examples, supra.

Procedure: Compound 25 (185 mg, 0.5 mmol) was dried by co-evaporation with dry pyridine (3×3 ml). It was then dissolved in dry pyridine (3 ml) and a solution of dimethoxytrityl chloride (222 mg, 0.57 mmol) in a 1:1 mixture of methylene chloride/pyridine (4 ml) was added dropwise with stirring. Stirring was continued for 1.5 hours, and the reaction was monitored by silica gel thin-layer chromatography using a methylene chloride/methanol (8:1) solvent system. The reaction was quenched by addition of methanol (0.2 ml); stirring was continued for 10 minutes. The pyridine was evaporated under vacuum. The residue was dissolved in methylene chloride (150 ml) and washed with saturated aqueous sodium bicarbonate (2×50 ml) followed by water (50 ml). After drying over anhydrous $MgSO_4$, the methylene chloride solution was evaporated to dryness under vacuum. The residue was purified by silica gel flash chromatography using a methylene chloride/ethyl acetate (11:5) solvent system containing 0.1% pyridine according to the method described, supra. Fractions containing product were identified by silica gel thin-layer chromatography, as described above. These fractions were pooled and evaporated to dryness, giving 250 mg of 26 (75% yield).

(c) Synthesis of 1-0-(Dimethoxytrityl)-2-0-(N,N-Diisopropylamino-methoxyphosphinamido)-3-N-[N -(Fluorenylmethoxycarbonyl)-glycidyl]-Amino-1,2-Propanediol (21)

Materials: The materials are described in preceding examples, supra.

Procedure: Compound 21 (235 mg, 0.35 mmol) was dried by co-evaporation with dry pyridine (2×3 ml). It was then dissolved in dry methylene chloride (2 ml) and N,N-diisopropylethylamine (244 ul, 1.4 mmol) was added. Next, N,N-diisopropylamino-chloromethoxyphosphine (105 ul, 0.53 mmol) was added dropwise with stirring under an argon atmosphere. The reaction was found to have gone to completion after 20 minutes by silica gel thin-layer chromatography using a methylene chloride/ethyl acetate/triethylamine (10:5:0.5) solvent system. The reaction mixture was then diluted into ethyl with saturated aqueous sodium bicarbonate (2×25 ml). After drying over anhydrous $MgSO_4$, the ethyl acetate layer was evaporated under vacuum. The residue was redissolved in ethyl acetate (3 ml) and poured into hexanes (150 ml) at −25 degrees C. The precipitate was filtered and dried under vacuum to give 210 mg of 21 (72%). $^{31}$P-NMR ($CDCl_3$, in ppm relative to trimethylphosphate): 147.5 (d). The structure was also confirmed by $^1$H-HMR analysis.

EXAMPLE 3(C)

Synthesis of 3-N-(4-Aminobutyryl)-Amino-1,2-Propanediol and 3-N-(6-Aminocaproyl)-Amino-1,2-Propanediol Based Linker Reagents (22, 23)

Figure 7A:
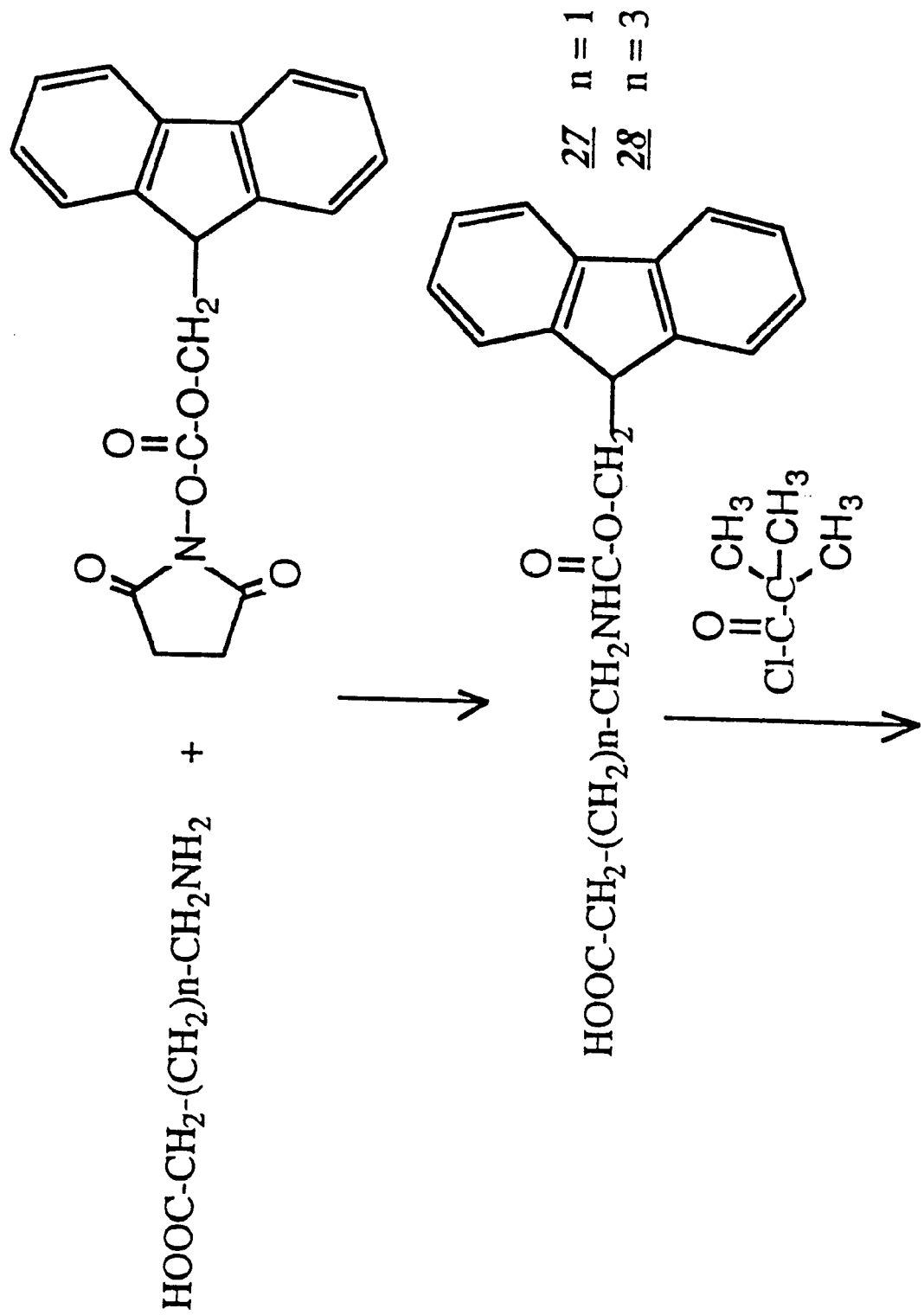
Figure 7B:
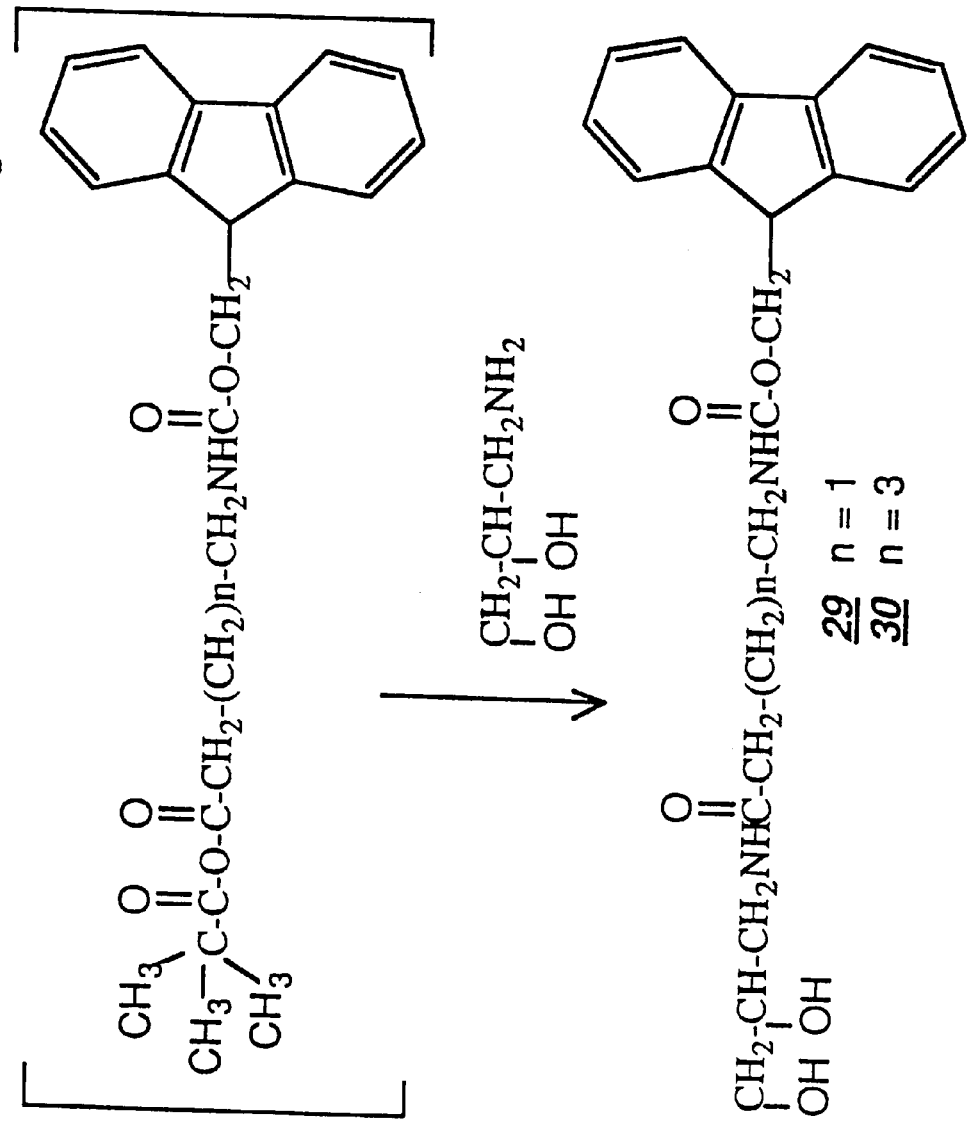

The steps of the syntheses which are unique to this example are diagrammed in FIG. 7 and are described below.

(a) Synthesis of N-Fluorenylmethoxycarbonyl Protected forms of 4-Aminobutyric Acid and 6-Aminocaproic acid (N-Fmoc-4-Aminobutyric Acid, 27, and N-Fmoc-6-Aminocaproic Acid, 28)

Materials: 4-aminobutyric acid and 6-aminocaproic acid were purchased from Aldrich Chemical Co. (Milwaukee, Mich., U.S.A.). Fmoc-NHS was described in Example 3(A).

Procedure: These syntheses were performed as described in the method of A. Paquet (*Can. J. Chem.*, 1982, 60, 976).

(b) Coupling of either of N-Fmoc-4-Aminobutyric Acid and N-Fmoc-6-Aminocaproic Acid with 3-Amino-1,2-Propanediol Materials: Trimethylacetyl chloride was purchased from Aldrich Chemical Co. (Milwaukee, Wis., U.S.A). Other materials are described in the preceding examples, supra.

Procedure: Either of compounds 27 and 28 (1 mmol) was first dried by co-evaporation with pyridine (2×3 ml). The residue was then dissolved in a mixture of dry dimethylformamide (3 ml) and dry tetrahydrofuran (3 ml). the resulting solution was cooled in an ice bath and N,N-diisopropylethylamine (1 mmol) was added, followed by slow addition of trimethylacetyl chloride (1 mmol) with stirring. Stirring was continued in an ice bath for 45 minutes. Next, a solution of 3-amino-1,2-propanediol (1.2 mmol) in dry dimethylformamide (3 ml) was added, and the resulting mixture was allowed to warm to room temperature and stirred for 1 hour. The reaction was monitored by silica gel thin-layer chromatography using a methylene chloride/methanol/acetic acid (10:1:0.1) solvent system. Based on this analysis, the reaction was determined to have gone to approximately 90% completion. The reaction mixture was then concentrated under vacuum, diluted with ethyl acetate (100 ml) and transferred to a separatory funnel. The organic solution was washed with saturated aqueous sodium bicarbonate (2×50 ml) and water (50 ml). After drying over anhydrous, $MgSO_4$, the organic layer was evaporated to dryness. Usually, the resulting product was determined to be in greater than 95% purity and was used in subsequent steps without further purification. In cases where purification was necessary, however, it was performed by silica gel flash chromatography as described in the preceding examples, supra, using a methylene chloride/methanol (40:1) solvent system. The purity of 29 and 30 were confirmed by $^1$H-NMR analysis.

(c) 1-0-Dimethoxytritylation of 29 and 30

The materials and procedure for this synthesis were as described in Example 3(B), part (b). The purity of these materials was confirmed by H-NMR.

(d) Conversion of the compounds referred to in part (c), above, to the corresponding 2-0-(N,N-diisopropylmethyl)-phosphoramidites (22 and 23)

The materials and procedure for this synthesis were as described in Example 3 (B), part (c). The purity of the products 22 and 23 was confirmed by $^{31}$P-NMR.

EXAMPLE 3 (D)

Figure 8A:
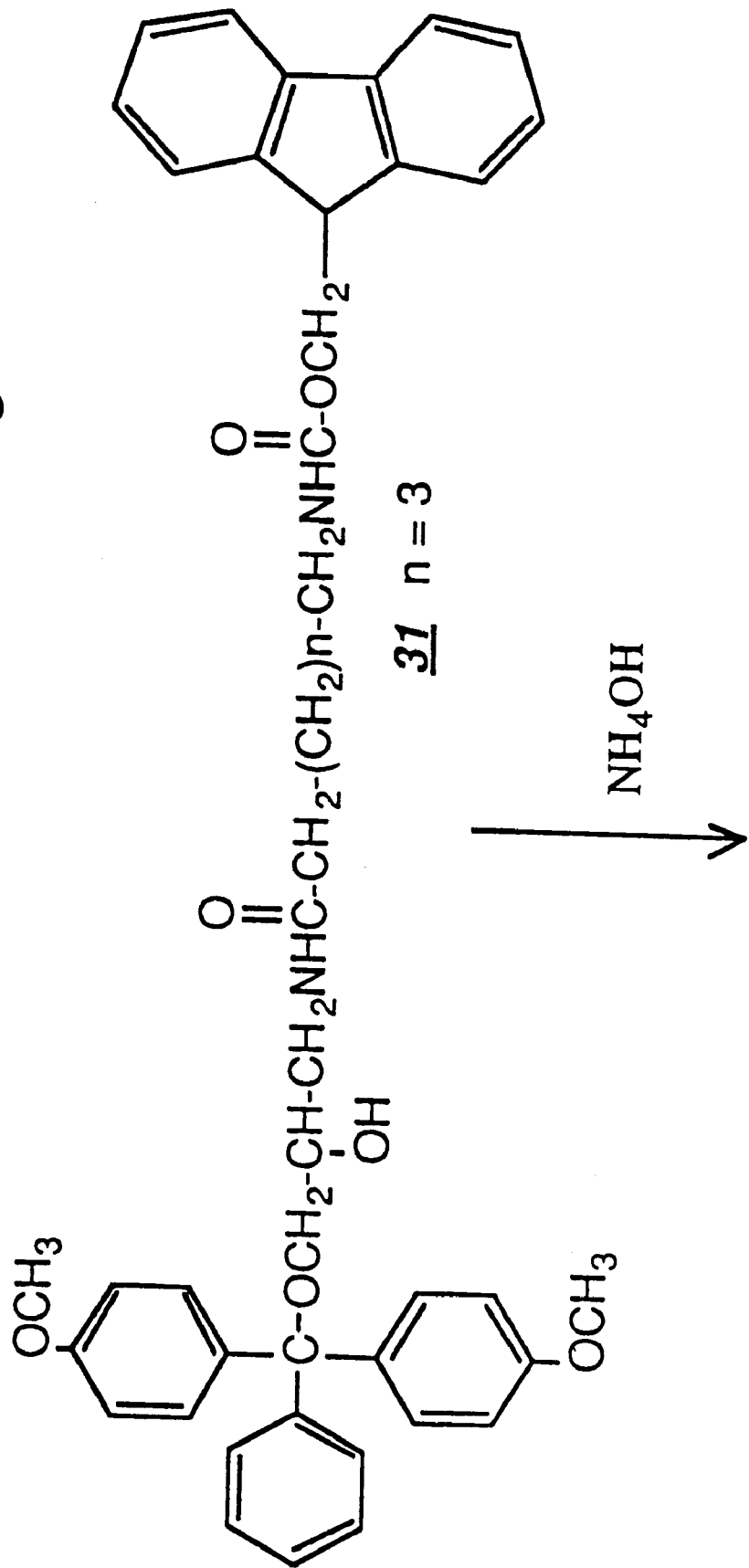
Figure 8B:
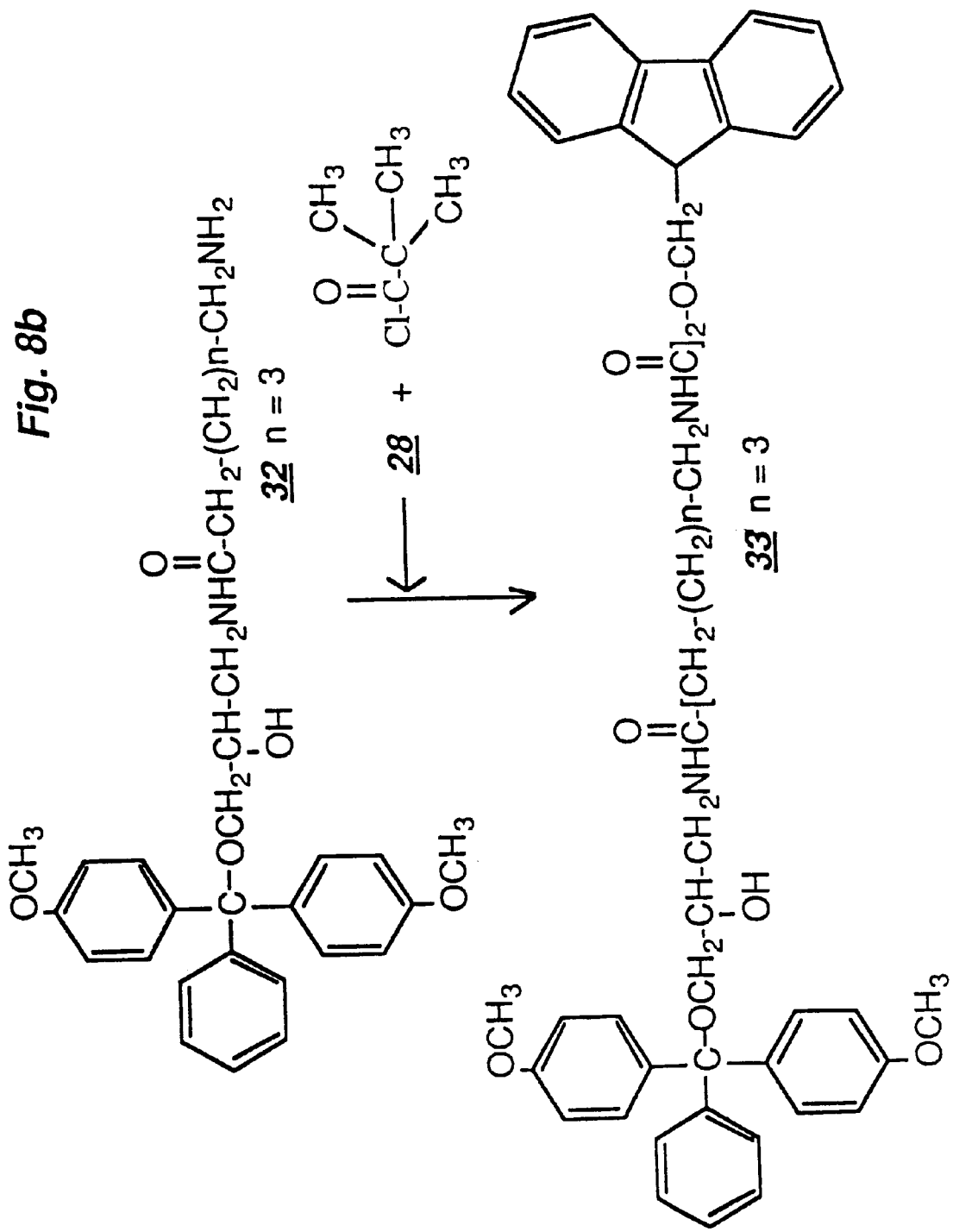

Synthesis of a Further Extended Analog of a 3-N-(6-Aminocaproyl)-Amino-1,2-Propanediol Based Linker Reagent The unique steps to this synthesis are diagrammed in FIG. 8 and are described below.

(a) Synthesis of 1-0-(Dimethoxytrityl)-3-N-(6-aminocaproyl)-Amino-1,2-Dihydroxypropane (32)

Materials: Compound 31 was prepared as described in Example 3 (C), part (c).

Procedure: Compound 31 (0.89 g, 1.1 mmol) was subjected to ammonolysis with concentrated ammonium hydroxide (10 ml) and pyridine (10 ml) at room temperature overnight. Aliquots from the reaction were spotted on silica gel TLC plates and treated with ninhydrin reagent to monitor deprotection of the primary amine. The reaction mixture was then taken to dryness under vacuum and the resulting residue (32) was used in the subsequent step without purification.

(b) Coupling of Compound 32 with Compound 28

Materials: Compound 28 was synthesized according to the procedure described in Example 3 (C), part (a).

Procedure: N-Fmoc-aminocaproic acid (28, 1.1 mmol) was reacted with trimethylacetyl chloride (1.1 mmol) according to the procedure described in Example 3(C), part (b), supra. Next, a solution of compound 32 (1.1 mmol) in dry dimethylformamide was added, again according to the procedure in Example 3(C) part (b). The resulting adduct, 32, was purified by silica gel flash chromatography as described in the preceding examples using a chloroform/methanol (30:1) solvent system. The yield of product was 250 mg (23%).

(c) Conversion of Compound 33 to the Corresponding 2-0-(N,N-diisopropylamino)-methoxyphosphoramidite (24)

Procedure: The method was essentially the same as the one described supra in Example 3(B), part (c). Thus, compound 32 (240 mg, 0.285 mmol) was reacted with N,N-diisopropylamino-chloromethoxyphosphine (73 ul, 0.371 mmol) in dry methylene chloride (3 ml) containing N,N-diisopropylethylamine (198 ul, 1.14 mmol). The reaction was processed by diluting it with 2% triethylamine in ethyl acetate (50 ml) and extracting with saturated aqueous sodium bicarbonate (25 ml) and water (25 ml). The resulting organic layer was dried over anhydrous sodium, sulfate, filtered, and evaporated. The residue was dissolved in several milliliters of ethyl acetate and precipitated into hexanes (150 ml) as described in the aforementioned example. The yield of 24 was 200 mg, the purity of which was confirmed by $^1$H- and $^{32}$P-NMR spectroscopy.

EXAMPLE 4

Automated Attachment of 2-(3-Aminopropyl)-1,3-Dihydroxypropane Based Linker to Synthetic Oligonucleotides The attachment of the linker reagent described in Example 1, which shall be termed hereafter "L1", to various synthetic oligonucleotides will now be described.

(a) The "L1" reagent was coupled at the 5'-end of a deoxyoligonucleotide. A deoxyoligonucleotide having the sequence "5'-GCTCGTTGCGGGACTTAACCCAACAT-3'" was synthesized on a controlled pore glass support with an Applied Biosystems, Inc., Model 380A DNA Synthesizer using standard phosphoramidite chemistry. The 5'-dimethoxytrityl group was removed and a solution of "L1" (0.1M) in dry acetonitrile was coupled two times using standard coupling cycles. The percent couplings of the first and second additions of "L1" were quantitated relative to the amount of full length deoxyoligonucleotide by measuring the absorbance at 498 nm of the dimethoxytrityl released at the end of each coupling cycle; these values were determined to be 29% and 42%, respectively. The 5'-(L1)- and 5'-(L1)-(L1)-oligonucleotides were purified by gel electrophoresis on a 20% polyacrylamide gel containing 7 M urea. The corresponding bands were visualized by UV shadowing and were estimated to migrate slower on the gel with spacings about 1.5 times that of the corresponding additional nucleotide spacings. These bands were excised and the linker modified deoxynucleotides were recovered and purified by standard methodologies.

(b) The "L1" reagent was coupled at the 3'-end of a deoxyoligonucleotide. for this synthesis, a teflon oxidizable solid support was used (Molecular Biosystems, Inc., San Diego, Calif., U.S.A., catalog #OSS-01). When a deoxyribonucleotide is cleaved from this support, the compound used during the first coupling cycle remains at the 3'-end along with a 3'-terminal phosphate group. A solution of "L1" (0.2 M) in dry acetonitrile was coupled to this support using three coupling cycles with standard phosphoramidite chemistry on an Applied Biosystems, Inc., Model 380A DNA Synthesizer. Next, a deoxyoligonucleotide sequence identical to that presented supra in part (a), immediately above, was added using the same coupling chemistry. Initial percent couplings with the "L1" reagent were determined as described above to be 40%, 63% and 63% for the first, second., and third couplings, respectively. Following removal of the terminal dimethoxytrityl group from the resulting trimer, a deoxyoligonucleotide having the same sequence as in 4(a) was attached using standard phosphoramidite chemistry. The support material was then removed from the synthesizer and treated with concentrated ammonium hydroxide at 55 degrees C. for 16 hours. Next, the support was washed three times with water and treated with 50 mM NaIO4 in 20 mM sodium phosphate buffer (pH 7.4) for 2.5 hours at room temperature. Finally, the support was washed several times with water and treated with a 10% aqueous solution of n-propylamine at 55 degrees C. for 3 hours. The resulting solution was applied to a 20% polyacrylamide gel containing 7 M urea and electrophoresed. The corresponding 3'-(L1)-(L1)-(L1) deoxyoligonucleotide was recovered as described above.

(c) "L1" was coupled at the 3'-end of a deoxyoligonucleotide having the sequence "5'-AAATAACGAACCCTTGCAGGTCCTTTCAACTTTGAT-3'".

The method of synthesis was the same as is described in part (b), except that a Biosearch Model 8750 DNA Synthesizer was used.

(d) "L1" was coupled at the 3'-end of a deoxyoligonucleotide having the sequence "5'-CAGTCAAACTCTAGCCATTACCTGCTAAAGTCATTT-3'".

Again, the method described in part (b) was used except that the automated portion of the synthesis was done on a Biosearch Model 8750 DNA Synthesizer.

(e) Hybridization and melting temperatures (Tm) of synthetic deoxyoligonucleotide probes containing 2-(3-aminopropyl)-1,3-dihydroxypropane linkers ("L1") inserted between nucleotide bases.

Materials: Two L1-derivatives of a 33-mer deoxyoligonucleotide probe were synthesized by similar methods to those described above: "L1-Insertion" possesses L1 inserted between nucleotide residues 21 and 22 (numbering from the 5' -end); "L1-Replacement" possesses L1 between nucleotide residues 20 and 22 as a replacement for residue 21. Both probes have sequences which are complementary to ribosomal RNA from Clamydia trachomatis (the "target rRNA"). The probes were labelled with $125_I$ by a standard protocol developed at Gen-Probe Inc.; hydroxyapatite (HAP) was from Behring Diagnostic, Calbiochem Division, La Jolla, Calif.; sodium dodecyl sulfate (SDS), sodium phosphate (mono and dibasic salts) and hydrochloric acid were reagent grade from Fisher Scientific Corp.; Betagel (liquid scintillation cocktail) was from WestChem, San Diego, Calif. Al other materials were reagent grade. Manipulations were performed in 1.5 ml screw-capped polypropylene Eppendorf tubes unless otherwise stated.

Hybridizations were performed as follows: 48 ul of 1 M sodium phosphate (pH 6.8), 10 ul of 1% SDS (v/v), 10 ul of $125_I$ labelled probe (about 200,000 CPM), 29.5 ul of water, and either 2.5 ul of rRNA solution (0.5 ug, "target") or 2.5 ul of water ("control") were mixed and incubated at 60 degrees C. for one hour. 10 ul aliquots were next diluted into 1 mil of 0.12 M sodium phosphate (pH 6.8)/ 0.02% SDS/ 0.02% sodium azide and vortexed for 5 seconds. The diluted aliquots were incubated in a water bath which was heated from room temperature to 80 degrees C.; aliquots were removed at specified temperatures and stored on ice. The samples were then passed through small column of hydroxyapatite equilibrated with 0.12 M sodium phosphate (pH 6.8)/ 0.02% SDS/ 0.02% sodium azide, and the eluents were counted by scintillation using standard procedures. (The percent of counts remaining bound to the column corresponds to hybridized probe). Tm values were calculated as the temperatures at which 50% of the initially formed hybrid was thermally denatured to single stranded species. Results:

| Probe | Tm |
| --- | --- |
| L1-Insert | 69° C. |
| L1-Replacement | 66° C. |

The data indicates that both probes hybridize to the target rRNA as expected, with the Tm of the "insertion" probe being about three degrees higher than that for the "replacement" probe.

EXAMPLE 5

The ability of "L1" modified deoxyoligonucleotides to be labelled with biotin and fluorescein was demonstrated (a) The 5'-(L1)- and 5'-(L1)-(L1)-modified deoxyoligonucleotides described supra in Example 4(a) ("5'-L1GCTCGTTGCGGGACTTAACCCAACAT-3'" and "5'-L1-L1-GCTCGTTGCCCCACTTAACCCAACAT-3'") were labelled with P-32.

Materials: Alpha-32p adenosine triphosphate was purchased from New England Nuclear (DuPont, Boston, Mass., U.S.A.). Terminal deoxynucleotidyl transferase (TdT) and 5×tailing buffer were products of Bethesda Research Laboratories (Gaithersburg, Md., U.S.A.).

20pmol OF 5'-(L1)-(L1) modified oligonucleotides were reacted with 16.5 pmol of alpha-P-32 adenosine triphosphate (specific activity 3000 Ci/mmol) and 40 units of TdT in 20 ul of 1×tailing buffer at 37° C. for one hour. The resulting P-32 labelled oligonucleotides were purified on a Nensorb-20 (TM) column (New England Nuclear, DuPont Corp., Boston Mass., U.S.A.) according to the manufacturer's procedure, which is incorporated herein by reference.

(b) The P-32 labelled 5'-(L1)-(L1)-oligonucleotides were reacted with biotin-E-aminocaproic acid N-hydroxysuccinimide ("Bio-X-NHS", Calbiochem-Behring Corp., San Diego, Calif. U.S.A.). Streptavidin-agarose was purchased from Bethesda Research Laboratories (Gaithersburg, Md., U.S.A.), and D(+) biotin was from Calbiochem-Behring Corp. (San Diego, Calif., U.S.A.).

1 pmol of each modified oligonucleotide described above was reacted with 2.5 mM Bio-X-NHS in 125 mM borate buffer (pH 9) containing 12.5% dimethylsulfoxide for 1.5 hours. Small aliquots of the resulting reaction mixtures were then tested for binding to streptavidin-agarose in 50 mM sodium phosphate (pH 7.4)/2 mM EDTA/0.5 NaCl either in the presence ("nonspecific bound") or absence ("specific bound") of 0.2 mg/ml D(+) biotin. Bound material was quantified by scintillation counting:

| OLIGOMER | % NONSPECIFIC BOUND | % SPECIFIC BOUND |
|---|---|---|
| 5'-(l1) | 0.3% | 71.8% |
| 5'-(L1)-(L1) | 0.5% | 90.3% |

The attachment of biotin to these L1-modified oligomers was also confirmed by electrophoresing aliquots of the above reaction mixtures on a 20% polyacrylamide/7 M urea gel. Representative bands were visualized by autoradiography, indicating nearly quantitative conversions to the biotinylated forms, which migrated slower than the non-biotinylated controls.

(c) The 3'-L1-modified deoxyoligonucleotides described in Example 4(c,d) ("5'-AAATAACGAACCCTTGCAGGTCCTTTCAACTTTG AT-L1-3'" and "5'-CAGTCAAACTCTAGCCATTACCTGCTAAAGTCATTT-L1-3'") were labelled with fluorescein isothiocyanate and biotin-X-NHS, respectively. The oligonucleotides were first kinased with [gamma-$^{32}$P] adenosine triphosphate using T4-polynucleotide kinase according to the procedure of Maxam and Gilbert (Proc. Natl. Acad. Sci. U.S.A., 1977, Vol. 74, p. 560), which is incorporated herein by reference.

The first modified oligonucleotide was reacted with fluorescein isothiocyanate (FITC, Sigma Chemical Co., St. Louis, Mo., U.S.A.). 40 pmol of this oligomer was treated with 90 mM FITC in 0.1 M borate buffer (pH 9) containing 90% DMSO for 12 hours. The reaction mixture was then electrophoresed on a 20% polyacrylamide/7M urea gel. Bands were visualized by autoradiography. The uppermost band from each lane was excised and the FITC labelled oligomer was recovered from the gel and purified.

A binding assay to an anti-FITC antibody derivatized solid support was used to confirm the attachment of fluorescein to the oligonucleotide described above. Anti-FITC magnetic microspheres were purchased from Advanced Magnetics, Inc. (Cambridge, Mass., U.S.A.), Cat. #4310. Aliquots of the purified $^{32}$P labelled, FITC modified oligonucleotide were mixed with 0.5 ml buffer solution (50 mM sodium phosphate, pH 7.4/2 mM EDTA/0.5 M NaCl) containing 20 ul of anti-FITC microspheres in the presence ("nonspecific binding") or absence ("specific binding") of 20 mM hydrolyzed FITC. After 1 hour, the microspheres were removed by magnetic separation and the supernates were counted by Cerenkov radiation to determine the amount of bound material:

PERCENT NONSPECIFIC BINDING: 0.1%
PERCENT SPECIFIC BINDING: 80.2%

The second modified oligonucleotide was reacted with biotin-X-NHS. 40 pmol of this oligomer was treated with 10 mM bio-X-NHA in 0.1 M borate buffer (pH 9) containing 20% DMSO for 1 hour. The resulting biotinylated oligomer was purified by polyacrylamide gel electrophoresis as described above. The presence of biotin attached to this oligonucleotide was confirmed by analysis of binding on streptavidin-agarose as described supra in this example:

PERCENT NONSPECIFIC BINDING: 0.3%
PERCENT SPECIFIC BINDING: 87.4%

EXAMPLE 6

Resistance of a 3'-L1-modified Deoxyoligonucleotide to Hydrolysis Catalyzed by a Phosphodiesterase Materials: Phosphodiesterase from *Crotalus-durissus* was purchased form Boehringer-Mannheim Biochemicals (Indianapolis Ind., U.S.A.). This enzyme catalyzed exonucleolytic cleavage from the 3'-end of an oligonucleotide. A synthetic deoxyoligonucleotide having the sequence "5'-AAATAACGAACCCTTGCAGGTCCTTTCAACTTT GAT-3'" was synthesized on an Applied Biosystems Model 380A DNA Synthesizer using standard phosphoramidite chemistry. A probe having the same sequence but with a 3'-L1 linker attached was synthesized according to the procedure given in Example 4.

Both oligonucleotides were kinased with $^{32}$P according to the method mentioned in Example 5. Approximately 350, 000 CPM of each labelled oligonucleotide was reacted in 10 ul of buffer (0.1 M Tris-HCl, pH 8.0/20 mM MgCl$_2$) containing either $3 \times 10^{-5}$ or $3 \times 10^{-6}$ unit of phosphodiesterase. 1.5 ul aliquots were removed at 5 min., 10 min., 15 min., and 30 min. time intervals; the reactions were quenched by addition of 3 ul of 0.1 N NaOH. Next, 5 ul of 90% formamide containing bromphenyl blue and xylanol XCFF dyes was added to each aliquot, and the resulting samples were electrophoresed on a 20% polyacrylamide/7M urea gel. The gel was then analyzed by autoradiography.

The 3'-L1 modified oligonucleotide was found to be greater than 95% resistant to phosphodiesterase catalyzed hydrolysis after 30 minutes with both concentrations of the enzyme tested. There was essentially no full length unmodified oligonucleotide visible on the gel, however, indicating that the enzyme normally cleaves the oligomer without a 3'-L1 group.

EXAMPLE 7

Automated Incorporation of 2,2-Di-(3-Aminopropyl)-1,3-Dihydroxypropane Based Linker Reagent into a Synthetic Oligonucleotide The incorporation of the linker reagent described in Example 2, termed hereafter "L2", was inserted between bases of a synthetic oligonucleotide, generating the sequence "5'-CGTTACTCGGATGCCCAAAT(L2) ATCGCCACATTCG-3'". The method used was similar to that described in Example 1(a), except that a solution of "L2" (0.1 M in acetonitrile) was reacted in the thirteenth coupling cycle, rather than in the last coupling cycle as described in Example 4(a). The efficiency of coupling with "L2" was about 30%, as estimated from the amount of dimethoxytrityl released (see Example 4(a)).

EXAMPLE 8

Automated Incorporation of 3-Amino-1,2-Propanediol Based Linker Reagent into a Synthetic Oligonucleotide The incorporation of this linker, termed hereinafter "L3", into a synthetic oligonucleotide having the sequence "5' CCCGCACGTCCCTATT(L3)AATCATTACGATGG-3'" was performed according to the procedure given in Example 4(a). In this example, a solution of "L3" (0.3 M in dry acetonitrile) was reacted in the fifteenth coupling cycle; the coupling efficiency of this step, estimated from dimethoxytrityl release (see Example 4(a)), was about 60%.

EXAMPLE 8(A)
Automated incorporation of linker reagents 20, 21, 22, 23 and 24 into Synthetic Oligonucleotides The incorporation of linker reagents 20–24, the synthesis of which is described above in Examples 3(A)–3(D), was performed as described above in Example 4, part (a). The corresponding linkers associated with these reagents are referred to hereafter as "L4", "L5", "L6", "L7" and "L8", respectively. Thus, in a particular instance corresponding to the use of one of the aforementioned reagents, a 0.12–0.2 M solution of the reagent in dry acetonitrile was-loaded in position #6 of an Applied Biosystems Model 380A DNA Synthesizer (Foster City, Calif., U.S.A.). The incorporation of the reagent into an oligonucleotide polymer was achieved using a standard phosphoramidite coupling protocol. A series of oligonucleotides were prepared, ranging from 17 to 35 bases in length, with each of the linkers L4–L8 inserted at various positions within the sequences. The coupling efficiencies associated with these reagents, as measured by trityl release at the end of the coupling cycle, ranged between 75% and 98%.

EXAMPLE 9
Labelling of Amine Linker-Arm Probe with Acridinium Ester and Subsequent Purification A 25 mM stock solution of acridinium ester (for composition refer to I. Weeks et al., Clin. Chem., Vol. 29, p. 1474, 1983) was prepared in distilled DMSO. The desired amount of a polymer produced in Examples 4, 7, or 8(A), was evaporated to dryness in a 1.5 ml conical polypropylene tube. The following cocktail was constructed by adding the following ingredients in the order listed:

3 ul $H_2O$ 1 ul 1 M HEPES (8.0)

4 ul DMSO (distilled)

2 ul 25 mM acridinium ester in DMSO (distilled)

The mixture was vortexed, spun in a microcentrifuge for 2 seconds (to bring the contents to the bottom of the tube), and incubated at 37° C. for 20 minutes. At that point, the following components were added to the reaction cocktail in the order listed:

3.0 ul 25 mM acridinium ester in DMSO (distilled)

1.5 ul $H_2O$ 0.5 ul 1 M HEPES (8.0)

The cocktail again was vortexed, spun, and incubated an additional 20 minutes at 37° C. The unreacted label was quenched using a 5-fold excess of lysine by adding 5 ul of 0.125 M lysene in 0.1 M HEPES (8.0), 50% DMSO, and incubated 5 minutes at room temperature.

At this point the acridinium ester-labelled oligomer was purified using the following method. To the 20 ul quenched reaction mixture 30 ul 3 M NaOAc (5.0), 245 ul $H_2O$ and 5 ul glycogen was added as a carrier (the glycogen was pre-treated to remove any nuclease activity). The sample was vortexed briefly and 640 ul of absolute EtOH was added. The sample was vortexed briefly and incubated on ice 5–10 minutes, then centrifuged 5 minutes at 15,000 rpm in a microcentrifuge. The supernatant was carefully removed and the pellet was redissolved in 20 71 of 0.1 M NaOAc (5.0), 0.1% SDS. The sample was further purified by ion-exchange high performance liquid chromatography (HPLC) as follows: the 20 ul redissolved pellet was injected onto a Nucleogen-DEAE 60-7 ion-exchange HPLC column mounted in an IBM 9533 HLPC system. All buffers used in the process were made with HPLC grade water, acetonitrile ($CH_3CN$) and sodium acetate (NaOAc), and reagent grade glacial acetic acid (HOAc) and LiCl. Additionally, all buffers were filtered through 0.45 um pore size Nylon –66 filters before use. In the specific case of a nucleotide/non-nucleotide multimer having a total of 26 monomeric units of which only one was non-nucleotide monomeric unit, the following elution protocol was employed. Buffer A was 20 mM NaOAc, pH 5.5, 20% $CH_3CN$; Buffer B was 20 mM NaOAc (pH 5.5), 20% $CH_3CN$, and 1 M LiCl. Elution was achieved with a linear gradient from 55% Buffer A, 45% Buffer B to 30% Buffer A, 70% Buffer B in 25 minutes at a flow rate of 1 ml/min. Absorbance at 260 nm was monitored during the run; fractions of 0.5 ml were collected in 1.5 ml conical polypropylene tubes. Immediately after the run, 5 ul of 10% SDS was added to each tube followed by vortexing of each tube (this was done to ensure that the acridinium ester-labelled probe did not stick to the walls of the tube). A 0.5 ul aliquot was removed from fractions 21–42 and added to 200 ul water in a 12×75 mm tube (a separate pipet tip was used for each aliquot to avoid a carryover problem). The chemiluminescence of each aliquot was then determined in a Berthoid Clinilumat by automatic injection of 200 ul of 0.25 N $HNO_3$, 0.1% $H_2O_2$, followed after a 1 second delay by 200 ul of 1N NaOH and reading of chemiluminescence for 10 seconds.

Fractions 29–33 were EtOH precipitated by adding to each 5 ul glycogen, to each, vortexing, adding 1 ml EtOH to each vortexing, incubating 5–10 minutes on ice, and centrifuging 5 minutes at 15,000 rpm in a microcentrifuge. Each supernatant was carefully removed, each pellet was redissolved in 20 ul 0.1 M NaOAc, pH 5, 0.1% SDS and these separate fractions were then pooled.

It has been demonstrated by the above examples then, that reagents of the present invention can be prepared, each of which has a non-nucleotide skeleton, first and second coupling groups, and a ligand, all as previously described under the "Summery of the Invention." In particular, reagent (5) has a non-nucleotide propyl skeleton, to which is bonded a first coupling group of methyl-N,N-diisopropylphosphoramido, a second coupling group of a 1-hydroxy protected by dimethoxytrityl (DMT), and a ligand in the form of the aminopropyl linking arm which is protected by the trifluoroacetyl. Reagent (10) is the same as reagent (5), except that the former is provided with two identical ligands (in the form of the two protected linking arms trifluoroacetylaminopropyl). Reagent (13) is also similar to reagent (5), except that the non-nucleotide skeleton is an ethyl rather than a propyl, and the linking arm is shorter in length, being only a trifluoroacetyl protected methylamine rather than a similarly protected aminopropyl.

As also demonstrated above, a single reagent of the present invention can be used to provide a linking arm specifically at any preselected position(s) only, on a nucleotide multimer, without introducing unwanted nucleotides. As also has been described, by coupling a skeleton to a nucleotide and another skeleton, (which is in turn then coupled to another skeleton, and so on to produce a chain), the reagents of the present invention now allow the possibility of a series of adjacent ligands (e.g., labels or linking arms to which labels can be attached) being provided in a nucleotide multimer. Thus, multiple adjacent labels can be linked to the probe, thereby enhancing sensitivity of a hybridization assay using such a probe.

Furthermore, the use of one, or a series of sequentially linked non-nucleotide skeletons of the present invention can additionally serve to bridge between two nucleotide sequences on the probe which are complementary to corresponding sequences on a target nucleotide multimer, which may be bridged by a single different nucleotide or a different sequence in a test sample. Thus, the target nucleotide multimer may actually be a group of two or more nucleotide multimers consisting of common nucleotide sequences of interest, which are bridged by a single different nucleotide or differing nucleotide sequences not of interest. Even when a single target sequence is of interest, it is possible to prepare the probe with a complementary sequence with the non-nucleotide monomeric unit bearing the labelling group, coupled between any two nucleotides. In such case, the probe hybridizes the target nucleotide sequence in a normal manner except that the monomeric unit bearing the labelling group will tend to conform itself in such a manner as to not interfere with the foregoing hybridization (i.e., that is it will tend to "loop out" of the hybrid structure). Such an arrangement can be particularly advantageous in situations where it is desireable to take advantage of intercalation effects (as described by U. Asseline et al, Proc. Natl. Acad. Sci. U.S.A., v. 81, pp 3297–3301), for example, to perhaps increase probe specificity. Of course, the fact that the present invention uses non-nucleotide monomeric units, considerably reduces interference of the type previously described, in connection with prior probes which use nucleotide monomeric units.

As discussed in the "Summary of the Invention" above, compounds (4), (9), and (12) can be attached to a solid-phase synthesis support through their primary hydroxyl groups (see Gait and Sarang texts, supra. on techniques which can be adapted for such a purpose). The resulting derivatized supports, when used for additional polymer synthesis, result in the attachment of a non-nucleotide monomeric unit at the 3'-terminus of the resulting nucleotide/non-nucleotide polymer.

It will be appreciated that numerous variations to the above described invention, are possible. For example, the ligand can actually be a label or an intercalator which is provided on the reagents of the present invention, prior to their being coupled to a nucleotide of a nucleotide multimer. Further, as described in the "Summary" above, various other protecting groups can be used other than those of the specific Examples above. However, the use of either of the trifluoroacetyl and 9-fluorenylmethoxycarbonyl amino protecting groups is particularly preferred, since it is cleaved to deprotect the amine under the same alkaline conditions as used in known standard oligonucleotide synthesis, to deprotect exocyclic nucleotide amines (typically concentrated $NH_4OH$ at 50° C. for 1 to 12 hours). Likewise, the use of dimethoxytrityl 5' hydroxy protection, methyl or beta-cyanoethyl phosphite O protection, and N,N-diisopropyl as a phosphite leaving group during coupling, all allow the reagents to be fully compatible with presently standard oligonucleotide solid-phase synthesis techniques, so as to minimize the need for any additional special steps.

Other variations and alterations of the above defined embodiments of the invention will be conceivable to those skilled in the art. Accordingly, the invention is not limited to those embodiments described in detail above.

We claim:

1. A linking reagent having the formula:

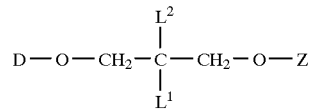

wherein:
D is a protecting group which may be removed to permit said linking reagent to be coupled to a second nucleotide;
$L^1$ is a first linker-arm having the formula:

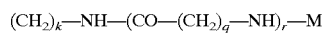

wherein M is a protecting group, or a label stable to DNA synthesis and deprotection conditions,
k is an integer between 1 and 4, inclusive,
q is an integer between 1 and 11, inclusive,
r is either 0, 1, or 2, provided that k+1+(2+q)r is an integer between 1 and 25 inclusive;
$L^2$ is H or $L^1$; and
Z is H, a cleavable ester attached to a DNA synthesis support, or a reactive phosphorus-containing group able to couple to or activatable for coupling to an OH group of a first nucleotide.

2. The linking reagent of claim 1, wherein Z is said reactive phosphorus-containing group.

3. The linking reagent of claim 1, wherein Z has the formula:

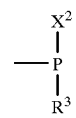

wherein,
$X^2$ is either a halogen or a substituted amino; and
$R^3$ is selected from the group consisting of alkyl, alkoxy and phenoxy.

4. The linking reagent of claim 3, wherein $X^2$ is either Cl or a secondary amino; and
$R^3$ is selected from the group consisting of methoxy, ethoxy, and beta-cyanoethoxy.

5. The linking reagent of claim 4, wherein $X^2$ is selected from the group consisting of diisopropylamino, dimethylamino and morpholino.

6. The linking reagent of claim 4, wherein $X^2$ is selected from the group consisting of diisopropylamino and dimethylamino; and
$R^3$ is selected from the group consisting of methoxy and beta-cyanoethoxy.

7. The linking reagent of claim 6, wherein r=0.
8. The linking reagent of claim 7, wherein k=3.
9. The linking reagent of claim 8, wherein M is fluorenylmethoxycarbonyl or trifluoroacetyl.
10. The linking reagent of claim 9, wherein D is selected from the group consisting of trityl and dimethoxytrityl.
11. The linking reagent of claim 8, wherein M is trifluoroacetyl and D is dimethoxytrityl.

12. The linking reagent of any one of claims 5–11 wherein $L^2$ is H.

13. A linking reagent having the formula:

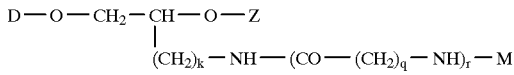

wherein:
- D is a protecting group which may be removed to permit said linking reagent to be coupled to a second nucleotide;
- k is an integer between 1 and 4, inclusive;
- q is an integer between 1 and 11, inclusive;
- r is either 0, 1, or 2, provided that k+1+(2+q)r is an integer between 1 and 25 inclusive;
- M is a protecting group, or a label stable to DNA synthesis and deprotection conditions; and
- Z is H, a cleavable ester attached to a DNA synthesis support, or a reactive phosphorus-containing group able to couple to or activatable for coupling to an OH group of a first nucleotide.

14. The linking reagent of claim 13, wherein Z is said reactive phosphorus-containing group.

15. The linking reagent of claim 13, wherein Z has the formula:

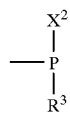

wherein,
- $X^2$ is either a halogen or a substituted amino;
- $R^3$ is selected from the group consisting of alkyl, alkoxy and phenoxy.

16. The linking reagent of claim 15, wherein $X^2$ is either Cl or a secondary amino; and
$R^3$ is selected from the group consisting of methoxy, ethoxy, and beta-cyanoethoxy.

17. The linking reagent of claim 16, wherein $X^2$ is selected from the group consisting of diisopropylamino, dimethylamino and morpholino.

18. The linking reagent of claim 16, wherein $X^2$ is selected from the group consisting of diisopropylamino and dimethylamino; and
$R^3$ is selected from the group consisting of methoxy and beta-cyanoethoxy.

19. The linking reagent of claim 18, wherein r=0.

20. The linking reagent of claim 19, wherein k is 1.

21. The linking reagent of claim 19, wherein k is 4.

22. The linking reagent of claim 18, wherein r is 1.

23. The linking reagent of claim 22, wherein q is an integer between 1 and 5, inclusive.

24. The linking reagent of claim 23, wherein k is 1.

25. The linking reagent of claim 18, wherein k is 1, r is 1, and q is 1.

26. The linking reagent of claim 18, wherein k is 1, r is 1, and q is 3.

27. The linking reagent of claim 18, wherein k is 1, r is 1, and q is 5.

28. The linking reagent of claim 18, wherein k is 1, r is 2, and q 5.

29. The linking reagent of any one of claims 19–28, wherein M is trifluoroacetyl or fluorenylmethoxycarbonyl.

30. The linking reagent of claim of claim 29, wherein D is selected from the group consisting of trityl and dimethoxytrityl.

31. The linking reagent of any one claims 19–21, wherein M is trifluoroacetyl and D is dimethoxytrityl.

32. The linking reagent of any one claims 22–28, wherein M is dimethoxytrityl and D is dimethoxytrityl.

* * * * *